(12) United States Patent
Nagare et al.

(10) Patent No.: US 7,049,462 B2
(45) Date of Patent: May 23, 2006

(54) PRODUCTION PROCESS FOR PRODUCT OF DEHYDRATION REACTION AND APPARATUS USED FOR THE PRODUCTION

(75) Inventors: Koichiro Nagare, Yokohama (JP); Toru Uno, Yokohama (JP); Yoshiyuki Onda, Tokyo (JP); Tsutomu Yuasa, Osaka (JP); Masato Nishiue, Yokohama (JP); Hisamoto Kawano, Kawasaki (JP)

(73) Assignee: Nippon Shokubai Co., Ltd., Osaka (JP)

( * ) Notice: Subject to any disclaimer, the term of this patent is extended or adjusted under 35 U.S.C. 154(b) by 25 days.

(21) Appl. No.: 09/993,621

(22) Filed: Nov. 27, 2001

(65) Prior Publication Data

US 2002/0099165 A1      Jul. 25, 2002

(30) Foreign Application Priority Data

Nov. 28, 2000   (JP)   ............................. 2000-361896

(51) Int. Cl.
  *C07C 69/52*   (2006.01)
(52) U.S. Cl. .................. 560/205; 560/220; 560/221
(58) Field of Classification Search .................. 560/8, 560/76, 100, 129, 205
  See application file for complete search history.

(56) References Cited

U.S. PATENT DOCUMENTS 6,265,495 B1 *   7/2001   Hirata et al.

FOREIGN PATENT DOCUMENTS

| EP | 0 989 109 A1 | 3/2000 |
|---|---|---|
| WO | WO 98/56748 A1 | 12/1998 |
| WO | WO 00/64850 A1 | 11/2000 |

* cited by examiner

*Primary Examiner*—Johann Richter
*Assistant Examiner*—Karl Puttlitz
(74) *Attorney, Agent, or Firm*—Sughrue Mion, PLLC

(57) ABSTRACT

It is an object of the present invention to provide a production method of a dehydration reaction product by which the occurrence of troubles in the production step or the degradation in performance characteristics or quality of various chemical products can be suppressed to a satisfactory extent.

A production method of a dehydration reaction product
  which comprises a dehydration reaction step of subjecting a reaction solution containing a polymerizable compound to the dehydration reaction,
  said dehydration reaction step comprising using a dehydration reaction apparatus,
  said dehydration reaction apparatus comprising a reaction vessel, a condenser and a connecting pipe joining said reaction vessel with said condenser and satisfying the requirement:

$$0.05 < (B^3/A) < 35$$

where A is a capacity ($m^3$) of said reaction vessel and B is a total length (m) of said connecting pipe on the horizontal basis.

15 Claims, 10 Drawing Sheets

(a)

(b)

(c)

(d)

(e)

PRODUCTION PROCESS FOR PRODUCT OF DEHYDRATION REACTION AND APPARATUS USED FOR THE PRODUCTION

TECHNICAL FIELD

The present invention relates to a method of producing dehydration reaction products by subjecting a reaction solution containing a polymerizable compound to a dehydration reaction, a method of producing dehydration reaction products to be used in a production of polymers for cement additives, a method of producing dehydration reaction products which comprises a dehydration reaction step in which an alcohol and/or an amine and (meth) acrylic acid are subjected to esterification and/or amidation in the presence of a dehydrating solvent, and a dehydration reaction apparatus to be used therefor as well as a method of producing cement additives obtainable by using the dehydration reaction products.

PRIOR ART

Methods of producing dehydration reaction products which comprise a dehydration reaction step have been applied to the production of various esters, amides and the like, which are formed by a reaction involving a dehydration reaction, such as esterification or amidation. Such esters, amides and the like are useful as materials for the production of various polymers, for example as (meth) acrylic ester monomers or (meth)acrylamide monomers. Such polymers are to be suitably used, for example, in such chemical products as cement additives (cement dispersants), dispersants for pigments such as calcium carbonate, carbon black and inks, scaling inhibitors, dispersants for gypsum-water slurries, dispersants for coal-water slurries (CWM), thickening agents and the like.

Meanwhile, in dehydration reaction steps, the esterification reactions and amidation reactions are reactions in which chemical equilibrium is reached, so that, without removing byproduct water from the reaction system, namely when byproduct water is accumulated in the reaction system, the reaction yielding an esterification or amidation product will not proceed. Therefore, it is a general practice to use a dehydrating solvent and remove the byproduct water by distillating thereof with that solvent (azeotropic distillation). For example, a procedure generally followed comprises carrying out the reaction while separating and removing the byproduct water from the distillate and returning the dehydrating solvent to the reaction system and, after completion of the reaction, removing the dehydrating solvent by distilling off the solvent from the reaction vessel containing the esterification or amidation product.

Japanese Kokai Publication Hei-09-328346 discloses, in Comparative Examples 1 and 2, a method of synthesizing desired esterification products which comprises charging a reaction apparatus, prepared by providing a reaction vessel (separable flask) with a thermometer, stirrer and water separator to thereby make it possible to separate byproduct water, with methacrylic acid and methoxypolyethylene glycol (average number of moles of oxyethylene groups added: 10 moles) as starting materials, together with sulfuric acid (Comparative Example 1) or paratoluenesulfonic acid (Comparative Example 2) as an acid catalyst, phenothiazine as a polymerization inhibitor and cyclohexane as a dehydrating solvent, allowing the esterification reaction to proceed by heating the mixture with stirring while refluxing cyclohexane and allowing a cyclohexane-water azeotrope to distill out under ordinary pressure and removing the byproduct water using a water separator and, after completion of the esterification reaction, distilling off the cyclohexane used.

In such a production method, a condenser, for example a vertical multitubular heat exchanger, is used in distilling off an azeotrope (distillate) composed of the solvent and byproduct water and condensing the same or in distilling off the solvent. When such a vertical multitubular heat exchanger is used, as shown in FIG. 9, the distillate is introduced, as an intratubular fluid, into a plurality of heat exchanger tubes connected to upper and lower tubesheets, the intratubular fluid is subjected to heat exchange with the extratubular fluid, which is a cooling liquid, and the resulting liquefied and condensed distillate is discharged from the end of each heat exchanger tube of the vertical multitubular heat exchanger and fed to the water separator.

However, in such a production method, there arises a problem, namely a gel-like matter is formed during the production of the dehydration reaction product, for example in the step of distilling off and condensing an azeotrope composed of a solvent and byproduct water or in the step of distilling off a solvent. Some of such gel-like matter remains, as an impurity, in the reaction vessel and, when said impurity is adhering to the inside wall of such an apparatus as the condenser or of a connecting pipe, for instance, the fluid flow in the condenser or connecting pipe is prevented to be blocked, thus causing troubles in the production step. If the product is contaminated by it and the product is used as a starting material for the production of various polymers, it enters chemical products produced from those polymers and causes a deterioration of the performance characteristics or quality thereof. In the case of cement additives, which improve the fluidity of cement compositions and at the same time can improve the strength and durability and the like of hardened products, the deterioration in performance characteristics or quality as caused by the admixture of the impurity may possibly lead to decreases in strength and durability of civil engineering or architectural structures or like hardened matters to thereby causing problems such as decreased safety and increased cost of repairs.

Japanese Kokai Publication 2000-159881 discloses that the addition of an antigelling agent, and Japanese Kokai Publication 2000-30729 discloses a method which comprises warming (maintaining the temperature of) the connecting pipe between the reaction vessel and condenser by using a double pipe as the connecting pipe, for instance. However, these methods cannot satisfactorily prevent the occurrence of troubles in the production step as resulting from gel-like matter formation or the deteriorations in performance characteristics or quality of various chemical products. Thus, there is room for contrivance for improving the structure of the dehydration reaction apparatus constituted of a reaction vessel and a condenser so that the gel-like matter formation can be prevented to a satisfactory extent.

In production methods of dehydration reaction products which comprise such a dehydration reaction step, it is a conventional technique to allow the distillate to condense and liquefy in a condenser, allow an interface to appear between the dehydrating solvent and byproduct water using a water separator and reflux the dehydrating solvent while removing the byproduct water. On the occasion of the distillate liquefied and condensed in the condenser being discharged into the water separator, there arise the following problems.

Thus, (A) if a distillate-discharging opening is provided in the gaseous phase section of the water separator, the interface will fluctuate upon impacts of the distillate arriving at the liquid surface, making it impossible to detect the interface between the dehydrating solvent and byproduct water with sufficient accuracy. Conversely, if the discharge opening is provided in the liquid phase section of the water separator, not only the interface will fluctuate but also a pressure will be exerted on the discharge opening when the distillate is discharged; the pipe inside connecting the reaction vessel to the discharge opening via the condenser is placed in an reduced pressure state at the moment of discharge, upon which a pressure fluctuation occurs within the reaction vessel to cause bumping of the reaction solution in the reaction vessel. (B) The interface cannot be detected with sufficient accuracy. In particular when the amount of byproduct water is small or the liquid surface fluctuates, it is difficult to detect the interface with sufficient accuracy. (C) In a level gauge attached to the water separator, the substantial liquid replacement is slight, hence the liquid retention tends to result in formation of a gel-like matter as a result of polymerization of a polymerizable monomer, such as (meth)acrylic acid, distilling out together with the dehydrating solvent and byproduct water, hence in failure of the level gauge to function. If such problems arise, it will become no longer possible to produce the dehydration reaction product in a stable manner and, in addition, the safety will decrease, the cost of repairs will increase and, accordingly, the cost of production of the dehydration reaction product will increase.

In view of the above-mentioned state of the art, it is an object of the present invention to provide a production method of a dehydration reaction product by which the occurrence of troubles in the production step or the degradation in performance characteristics or quality of various chemical products can be suppressed to a satisfactory extent (1) by suppressing the formation of a gel-like matter to a satisfactory extent while removing byproduct water from the reaction system in the production method of a dehydration reaction product which comprises a dehydration reaction step of subjecting a reaction solution containing a polymerizable compound to the dehydration reaction, (2) by suppressing the formation of a gel-like matter in a vertical multitubular heat exchanger to a satisfactory extent in the production method of a dehydration reaction product to be applied to a production of a polymer for cement additives, which comprises a dehydration reaction step of using the vertical multitubular heat exchanger or (3) by preventing the reaction mixture from bumping while removing byproduct water from the reaction system, improving and stabilizing the accuracy in detecting the interface between the dehydrating solvent and byproduct water and, further, suppressing the formation of a gel-like matter to a satisfactory extent in the production method of a dehydration reaction product which comprises a dehydration reaction step of subjecting an alcohol and/or an amine with (meth)acrylic acid to esterification and/or amidation in the presence of a dehydrating solvent.

SUMMARY OF THE INVENTION

The present inventors made intensive investigations in an attempt to produce high-quality dehydration reaction products with high efficiency and, as a result, they first observed that while the gel-like matter formation is inhibited in the reaction solution in which a polymerization inhibitor is normally present, a gel-like matter is formed in a liquid retention area, namely a liquid retention area for the distillate distilled from the reaction vessel, where the polymerization inhibitor cannot act, if such area appears in the dehydration reaction apparatus used in the dehydration reaction step and they found that the dehydration reaction apparatus maybe contrived so that the formation of such a liquid retention area as resulting from the use of the dehydration reaction apparatus is prevented to a sufficient extent. More specifically, they realized that the formation of a liquid retention area can be inhibited and the above-mentioned problems can successfully be solved by (1) selecting certain parameters of the connecting pipe joining the reaction vessel with the condenser so that the value calculated according to a specific formula may be within a certain specific range and (2) providing the connecting pipe with a gradient. They also realized that when a vertical multitubular heat exchanger is used as a condenser, the formation of a liquid retention area can be inhibited and the above-mentioned problems can successfully be solved (1) by giving a structure to certain specific sites within the vertical multitubular heat exchanger so that no substantial retention areas for a distillate occur and (2) by constructing at least the tubesheet provided in the vicinity of the upper end out of the tubesheets provided in the vertical multitubular heat exchanger so that no substantial protrusions of the heat exchanger tubes occurs on the surface with which the distillate comes into contact.

They also found that while, in the conventional vertical multitubular heat exchangers as shown in FIG. 9, the heat exchanger tubes protrude on the tubesheet surface coming into contact with the distillate for the purposes, (1) of preventing leakage resulting from loosening of the connections between the tubesheets and heat exchanger tubes under the influence, on the heat exchanger tubes, of vibrations caused by the constant inflow and outflow of the intratubular fluid, namely the distillate from the reaction solution, and of the extratubular fluid, namely the cooling liquid, vibrations caused by the pump and compressor and vibrations directly caused by pulsations of rotating machines, (2) of making the connection sites between the respective tubesheets and heat exchanger tubes firm and strong and facilitating the installation of a large number of heat exchanger tubes and (3) of stably installing a large number of heat exchanger tubes which are made thin so that the surface area of contact with the cooling liquid may effectively be increased to thereby improve the efficiency of heat transfer. The above purposes (1) to (3) can be achieved even when the vertical multitubular heat exchanger to be used in the dehydration reaction step in producing, from a reaction solution, a dehydration reaction product to be applied to the production of polymers for cement additives is constructed so that there may exist no substantial retentive areas for the distillate on the tubesheet surface.

Furthermore, they found (A) that the reaction solution can be prevented from bumping to thereby stabilize the interface between the dehydrating solvent and byproduct water and improve the accuracy of detection thereof by contriving the feeding pipe to be attached to the water separator for use in a dehydration reaction step, (B) that the accuracy of detection of the interface between the dehydrating solvent and byproduct water can be improved by contriving the shape of the water separator and (C) that the detection device can be sufficiently prevented from being blocked with a gel-like matter by contriving the detection device to be attached to the water separator. More specifically, they realized that the above problems can successfully be solved by (1) designing the feeding pipe to be attached to the water separator so that it has an opening in the gaseous phase section and the liquid phase section in the water separator, (2) designing the shape of the water separator so that the lower portion thereof has a diameter smaller than that of the upper portion and the interface between the dehydrating solvent and byproduct water may be maintained in the lower portion and (3) causing an antigelling agent to act on inside of the detection device attached to the water separator.

It was also found that the products obtained by a production method of a dehydration reaction product using such a dehydration reaction apparatus, a vertical multitubular heat exchanger and a water separator are of high quality and therefore can be suitably used as starting materials for the production of polymers for cement additives and the like.

Thus, the present invention provides a production method of a dehydration reaction product which comprises a dehydration reaction step of subjecting a reaction solution containing a polymerizable compound to the dehydration reaction, said dehydration reaction step comprising using a dehydration reaction apparatus, said dehydration reaction apparatus comprising a reaction vessel, a condenser and a connecting pipe joining said reaction vessel with said condenser and satisfying the requirement:

$$0.05 < (B^3/A) < 35$$

where A is a capacity ($m^3$) of said reaction vessel and B is a total length (m) of said connecting pipe on the horizontal basis.

The invention further provides a production method of a dehydration reaction product to be applied to a production of a polymer for cement additives which comprises a dehydration reaction step of using a vertical multitubular heat exchanger in producing the dehydration reaction product from a reaction solution, said vertical multitubular heat exchanger exchanging heat between an extratubular fluid and a distillate from said reaction solution and having a structure comprising a body having an extratubular fluid inlet and an extratubular fluid outlet, covers provided at both upper and lower ends of said body, tubesheets provided in the vicinity of the both upper and lower ends of inside of said body and a plurality of heat exchanger tubes connected between said tubesheets, and no substantial retention areas for said distillate occurring on a connecting site between said tubesheet and said heat exchanger tube.

The invention further provides a production method of a dehydration reaction product to be applied to a production of a polymer for cement additives which comprises a dehydration reaction step of using a vertical multitubular heat exchanger in producing the dehydration reaction product from a reaction solution, said vertical multitubular heat exchanger exchanging heat between an extratubular fluid and a distillate from said reaction solution and having a structure comprising a body having an extratubular fluid inlet and an extratubular fluid outlet, covers provided at both upper and lower ends of said body, tubesheets provided in the vicinity of the both upper and lower ends of inside of said body and a plurality of heat exchanger tubes connected between said tubesheets, and no substantial protrusions of said heat exchanger tubes occurring on the surface, with which said distillate comes into contact, of at least the tubesheet provided in the vicinity of the upper end out of said tubesheets.

The invention still further provides a production method of a dehydration reaction product which comprises a dehydration reaction step of subjecting an alcohol and/or an amine with (meth)acrylic acid to esterification and/or amidation in the presence of a dehydrating solvent, said dehydration reaction step comprising using a reaction vessel and a water separator, said water separator being provided with a feeding pipe connected with said reaction vessel, and having a gaseous phase section and a liquid phase section therewithin, and said feeding pipe having openings in the gaseous phase section and in the liquid phase section.

The invention further provides a production method of a dehydration reaction product which comprises a dehydration reaction step of subjecting an alcohol and/or an amine with (meth)acrylic acid to esterification and/or amidation in the presence of a dehydrating solvent, said dehydration reaction step comprising using a reaction vessel and a water separator, and said water separator being provided with a feeding pipe connected with said reaction vessel, having a gaseous phase section and a liquid phase section therewithin, having smaller diameter in a lower portion thereof than a diameter in an upper portion and being so controlled that an interface between the dehydrating solvent and byproduct water is maintained in a lower portion thereof.

The invention still further provides a production method of a dehydration reaction product which comprises a dehydration reaction step of subjecting an alcohol and/or an amine with (meth)acrylic acid to esterification and/or amidation in the presence of a dehydrating solvent, said dehydration reaction step comprising using a reaction vessel and a water separator, said water separator being provided with a feeding pipe connected with said reaction vessel, having a gaseous phase section and a liquid phase section therewithin and being provided with a detecting device of an interface between the dehydrating solvent and byproduct water and/or a gas/liquid interface, and an antigelling agent being caused to act on inside of said detection device.

The invention also provides a dehydration reaction apparatus which is to be used in the above-mentioned production method of a dehydration reaction product.

EXPLANATION OF THE NUMERICAL SYMBOLS

Figure 1:
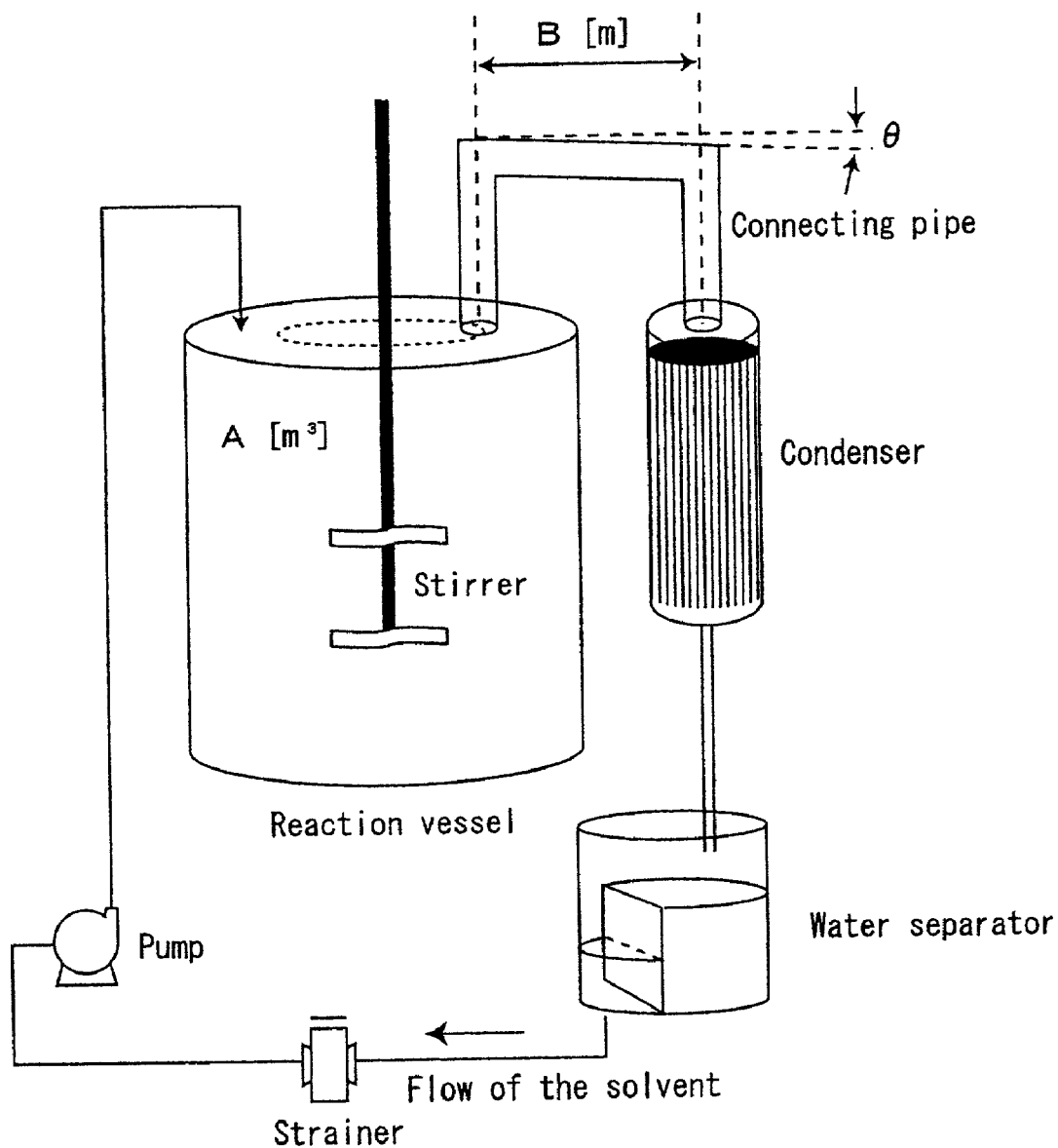
FIG. 1 is a schematic representation of an embodiment of the dehydration reaction apparatus according to the invention which comprises a reaction vessel, a condenser as well as a water separator.

1—extratubular fluid inlet
2—extratubular fluid outlet
3—intratubular fluid inlet
4—intratubular fluid outlet
5, 174—upper tubesheet
6, 175—lower tubesheet
7—top cover
8—rear cover
9, 173—heat exchanger tube
101—reaction vessel
102, 150—jacket
103—raw material alcohol storage tank
105—raw material (meth)acrylic acid storage tank
107—catalyst storage tank
109—polymerization inhibitor storage tank
111—neutralizing agent storage tank
113, 115, 117, 119, 121, 129, 130, 137, 139, 141, 145, 149, 153, 157, 161—piping
116, 160, 167, 169, 179—pump
123—connecting pipe
124—double pipe for keeping warmth
125, 128—condenser
126, 136—spray nozzle
127—water separator
129—feeding pipe (piping)
131—diaphragm (baffle plate)
133—section (A) in water separator
134—section (B) in water separator
135—treatment tank for byproduct water
136—level gauge (A)
138—level gauge (B)
140—control valve
142—circulation pump
143—dehydrating solvent storage tank
144—flow meter
147—antigelling agent storage tank
151—circulation route
155—vacuum pump
159—water-soluble antigelling agent storage tank
162—holes made on feeding pipe 129

DETAILED DESCRIPTION OF THE INVENTION

In the following, the present invention is described in detail.

The production method of a dehydration reaction product according to the invention comprises a dehydration reaction step of subjecting a reaction solution containing a polymerizable compound to the dehydration reaction. In ordinary modes of practice of such a production method of producing a dehydration reaction product, the dehydration reaction step is followed by a neutralization step, a step of solvent removal by distillation and so forth, as necessary.

First, the apparatus to be used in accordance with the invention in the above dehydration reaction step is described.

The above dehydration reaction step comprises using a dehydration reaction apparatus comprising a reaction vessel, a condenser and a connecting pipe joining said reaction vessel with said condenser. In such dehydration reaction apparatus, the dehydration reaction is carried out in the reaction vessel while a condensation and liquefaction procedure is carried out using the condenser.

In the above dehydration reaction step, other constituent(s) may be optionally used in addition to the reaction vessel, condenser and connecting pipe therebetween. In cases where the dehydration reaction involves a chemical equilibrium, a water separator is preferably connected to the condenser because the reaction proceeds well when the byproduct water resulting from the reaction is removed from the reaction vessel. In such a step, the following procedures are carried out: (1) the procedure, for facilitating the removal of the water formed in the reaction vessel, which comprises admixing a dehydrating solvent with the reaction solution according to need and causing azeotropy of said dehydrating solvent and water to give a vaporized distillate, (2) the procedure which comprises allowing said distillate to pass through a connecting pipe joining the reaction vessel with the condenser and to enter the condenser followed by condensing and liquefying the distillate in said condenser, (3) the procedure which comprises separating the condensed and liquefied distillate into the dehydrating solvent and water in the water separator connected with the condenser and (4) the procedure which comprises refluxing the dehydrating solvent separated into the reaction vessel. Typical examples of the apparatus constitution for carrying out such procedures are schematically shown in FIG. 1 and FIG. 2.

FIG. 1 shows an embodiment of a dehydration reaction apparatus which comprises a reaction vessel, a condenser as well as a water separator. Such a dehydration reaction apparatus is one of preferred embodiments of the present invention. In this embodiment, the apparatus comprises a reaction vessel, condenser, water separator, strainer and pump, together with pipings for connecting them. The connecting pipe joining the reaction vessel with the condenser has a shape such that the distillate coming out of the reaction vessel ascends, then goes toward the condenser and descends and enters the condenser. In this case, the distillate evaporated in the reaction vessel passes through the connecting pipe and enters the condenser, the distillate condensed and liquefied in the condenser is separated into the dehydrating solvent and water in the water separator. The byproduct water is thus removed from the reaction vessel while the dehydrating solvent is filtered through the strainer and refluxed to the reaction vessel by means of the pump.

Such a dehydration reaction apparatus is suitably applied to a relatively large-scale apparatus.

Figure 2:
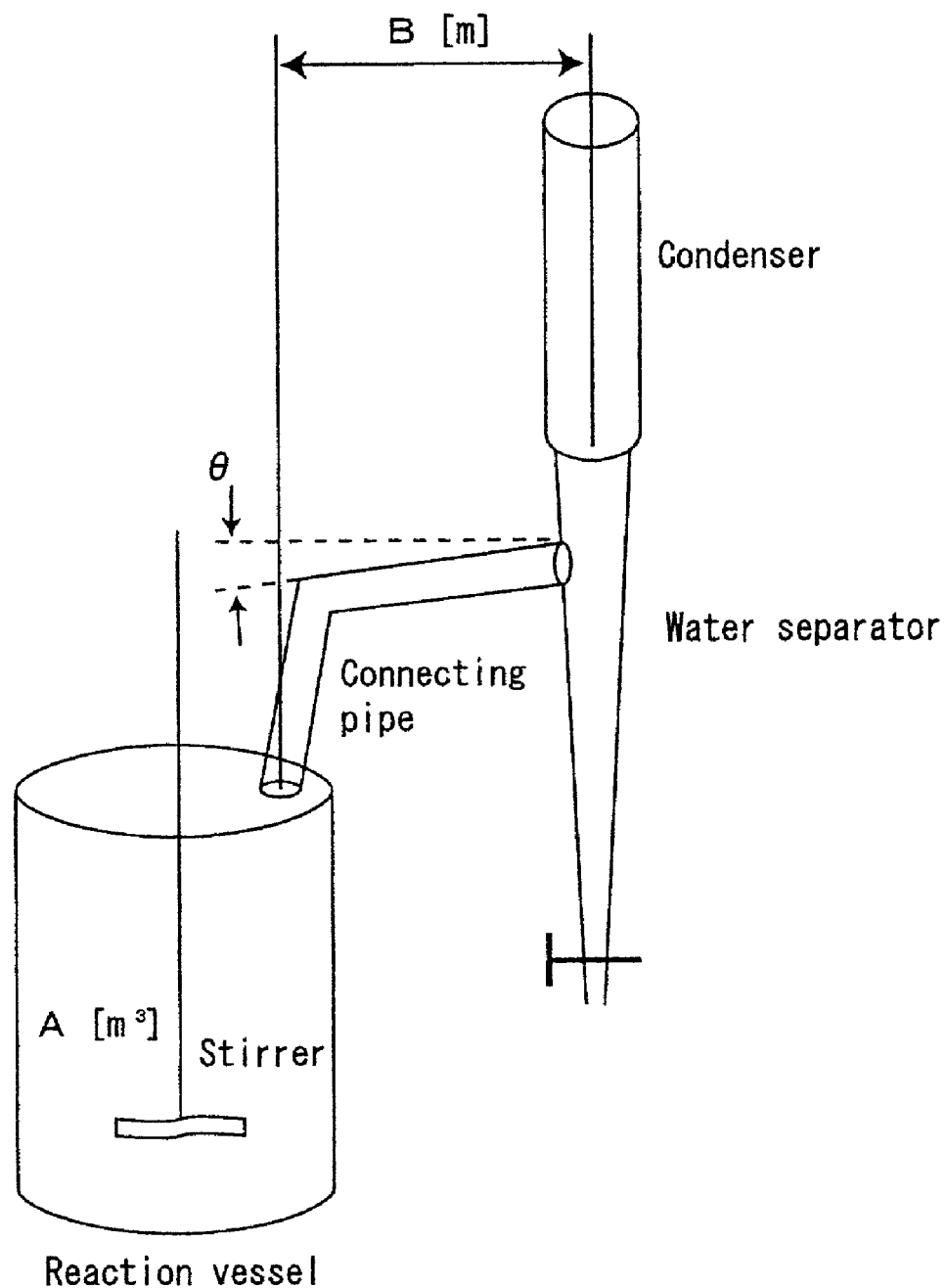
FIG. 2 is a schematic representation of another embodiment of the dehydration reaction apparatus according to the invention which comprises a reaction vessel, a condenser as well as a water separator.

In FIG. 2, too, is illustrated an embodiment of a dehydration reaction apparatus which comprises a reaction vessel, a condenser as well as a water separator. In this embodiment, the apparatus comprises a reaction vessel, condenser and water separator and a connecting pipe is provided for joining the reaction vessel with the condenser and the condenser is connected with the water separator. The connecting pipe joining the reaction vessel with the condenser has a shape such that the distillate coming out of the reaction vessel ascends, then goes toward the condenser and enters the condenser located at a higher level than the reaction vessel. In this case, the distillate evaporated in the reaction vessel passes through the connecting pipe and enters the condenser, and the distillate liquefied in the condenser is separated into the dehydrating solvent and water in the water separator. The byproduct water is thus removed from the reaction vessel. Such a dehydration reaction apparatus is suitably applied to a relatively small-scale apparatus.

The above reaction vessel has the same meaning as the reactor, reaction chamber, reaction kettle, etc. and includes all vessels in which a dehydration reaction can be carried out, without any particular limitation. The shape of the reaction vessel is not particularly restricted but may be polygonal pillar-like, cylindrical, or the like. In view of the agitating efficiency, handleability, versatility and the like, the cylindrical type is preferred, however. It may have or not have a baffle plate. The system for heating the reaction vessel may be one in which heating is carried out by contacting a heating medium, such as steam, with an external jacket or one in which heating is carried out by means of a heating apparatus, such as a coil, equipped inside the reaction vessel. The material of construction of the inside of such reaction vessel is not particularly restricted but may be any of such known materials as SUS. Preferred from the viewpoint of corrosion resistance are SUS 304, SUS 316 and SUS 316L. More preferred are SUS 316, SUS 316L and the like. The inside of the reaction vessel may be processed by glass lining or the like, so that it may be rendered inert to the starting reactants and products. Generally, such reaction vessel is equipped with a stirrer so that the dehydration reaction can be carried out homogeneously and efficiently. The stirrer is not particularly restricted. The stirrer generally comprises an electric motor, a shaft and a stirring blade(s). The stirring blades may be optional in shape. As the stirring blades, there may be mentioned desk turbines, fan turbines, curved fan turbines, herringbone turbines, multistage fan turbine blades, Pfaudler type impellers, Brumagin type, angled blades, propeller type, multiple blades, anchor type, gate type, double ribbon blades, screw blades, max blend blades and so forth. Among them, multistage fan turbine blades and Pfaudler type impellers are preferred because of their versatility.

The above-mentioned condenser is an apparatus for condensing and liquefying the distillate coming from the reaction vessel, and the above condensation/liquefaction is effected by heat exchange between the distillate and an extratubular fluid, namely, a cooling fluid. The "distillate" means all the matter distilled off from the reaction vessel by the dehydration reaction step and other steps. Thus, it includes byproduct water distilled off from the reaction vessel, byproduct water derived from a raw material charged as a form of an aqueous solution, the dehydration solvent used for azeotropic distillation with the byproduct water according to need and such starting reactants as (meth) acrylic acid distilled off and so on. As the form thereof, a gas and/or liquid can be mentioned.

The material of construction of the above condenser may be any of such known ones as SUS species, for example SUS 304, SUS 316 and SUS 316L, and carbon steel (CS) species. For further reducing the gel-like matter formation, the condenser inside may be mirror-finished or glass-lined. In view of the cost required for such processing or maintenance, the condenser made of SUS species such as SUS 304, SUS 316 or SUS 316L is preferably used, more preferably SUS 316 or SUS 316L. Even when such a condenser is used, the effects of the present invention can be produced.

The heat transfer area of the above condenser may vary depending on the capacity of the reaction vessel and other factors but is preferably 50 to 500 m$^2$, more preferably 100 to 200 m$^2$, for a reaction vessel of 30 m$^3$, for instance. The cooling medium to be used in such condenser includes, for example, water or an oil.

The capacity of the above water separator may vary depending on the capacity of the reaction vessel, the amount of the distillate and other factors but is preferably 1 to 20 m$^3$, more preferably 3 to 10 m$^3$, for a reaction vessel of 30 m$^3$, for instance.

The dehydration reaction apparatus to be used in the above dehydration reaction step satisfies the requirement:

$$0.05<(B^3/A)<35$$

where A is a capacity (m$^3$) of said reaction vessel and B is a total length (m) of said connecting pipe on the horizontal basis.

In accordance with the present invention, the capacity A (m$^3$) of the reaction vessel and the total length B (m) of the connecting pipe, on the horizontal basis, joining the reaction vessel with the condenser, as shown in FIG. 1 or FIG. 2, are selected so that the above requirement is satisfied. By doing so, the liquid retention possibly resulting in the formation of a gel-like matter within the piping connecting the reaction vessel with the condenser in the dehydration reaction step can be suppressed and the effects of the present invention are produced. If the value of B$^3$/A is not more than 0.05, the distance between the reaction vessel and the condenser will become too short and it will be unable to dispose them easily and also the apparatus maintenance will become difficult. If the value of B$^3$/A exceeds 35, a gel-like matter may be formed in the connecting pipe, so that the occurrence of troubles in the production step and/or the deterioration in performance characteristics or quality of various chemical products can no longer prevented. The relation to be satisfied is more preferably 0.05<(B$^3$/A)<2, still more preferably 0.1<(B$^3$/A)<1.

In the above dehydration reaction apparatus, the sites of joining the connecting pipe with the reaction vessel and condenser are not particularly restricted. One reaction vessel may be provided with one condenser or a plurality of condensers. From the dehydration reaction apparatus manufacturing cost viewpoint, however, one reaction vessel is preferably equipped with one condenser. In cases where one reaction vessel is equipped with a plurality of condensers, the respective condensers may be the same or different in type and the reaction vessel and the respective condensers may satisfy the above relation in the same manner or differently.

The capacity A (m$^3$) of the above reaction vessel, which means the capacity of the whole reaction vessel, is preferably 0.0001 to 100 m$^3$ in view of the possibility of reaction vessel manufacture and of the scale of dehydration reactions.

If it is less than 0.0001 m³, the dehydration reaction product may not be formed efficiently. If it exceeds 100 m³, it may become difficult to manufacture the reaction vessel. A more preferred capacity is 0.001 to 80 m³. For making the production method industrially efficient, the capacity is preferably 0.1 to 100 m³, more preferably 1.0 to 50 m³. The volume of the reaction solution in the reaction vessel is not particularly restricted but, from the viewpoint of stirring efficiency inside the reaction vessel and the like, it is preferably 5 to 95%, more preferably 20 to 90%, with the capacity of the whole reaction vessel being taken as 100%.

The above-mentioned total length B (m) of the connecting pipe on the horizontal basis means the total length, on the horizontal basis, from the distillate outlet of the reaction vessel to the distillate inlet of the condenser. In the case of FIG. 1 or FIG. 2, where one reaction vessel is provided with one condenser, for instance, the length is as illustrated in the figure. In cases where one reaction vessel is equipped with a plurality of condensers, the length is the sum of the lengths of the respective pipings on the horizontal basis. Thus, the length of the piping on the horizontal basis does not mean the beeline distance from the distillate outlet of the reaction vessel to the distillate inlet of the condenser but is the shortest distance between the vertical line drawn toward the center of the distillate outlet of the reaction vessel and the vertical line drawn toward the center of the distillate inlet of the condenser and the total length of the piping on the horizontal basis is the sum total of the lengths of the respective piping on the horizontal basis. The shape of the distillate outlet of the reaction vessel and of the distillate inlet of the condenser and the shape of the section of the connecting pipe is generally circular but is not particularly restricted. The center thereof is thus appropriately selected according to the shape.

Figure 3:
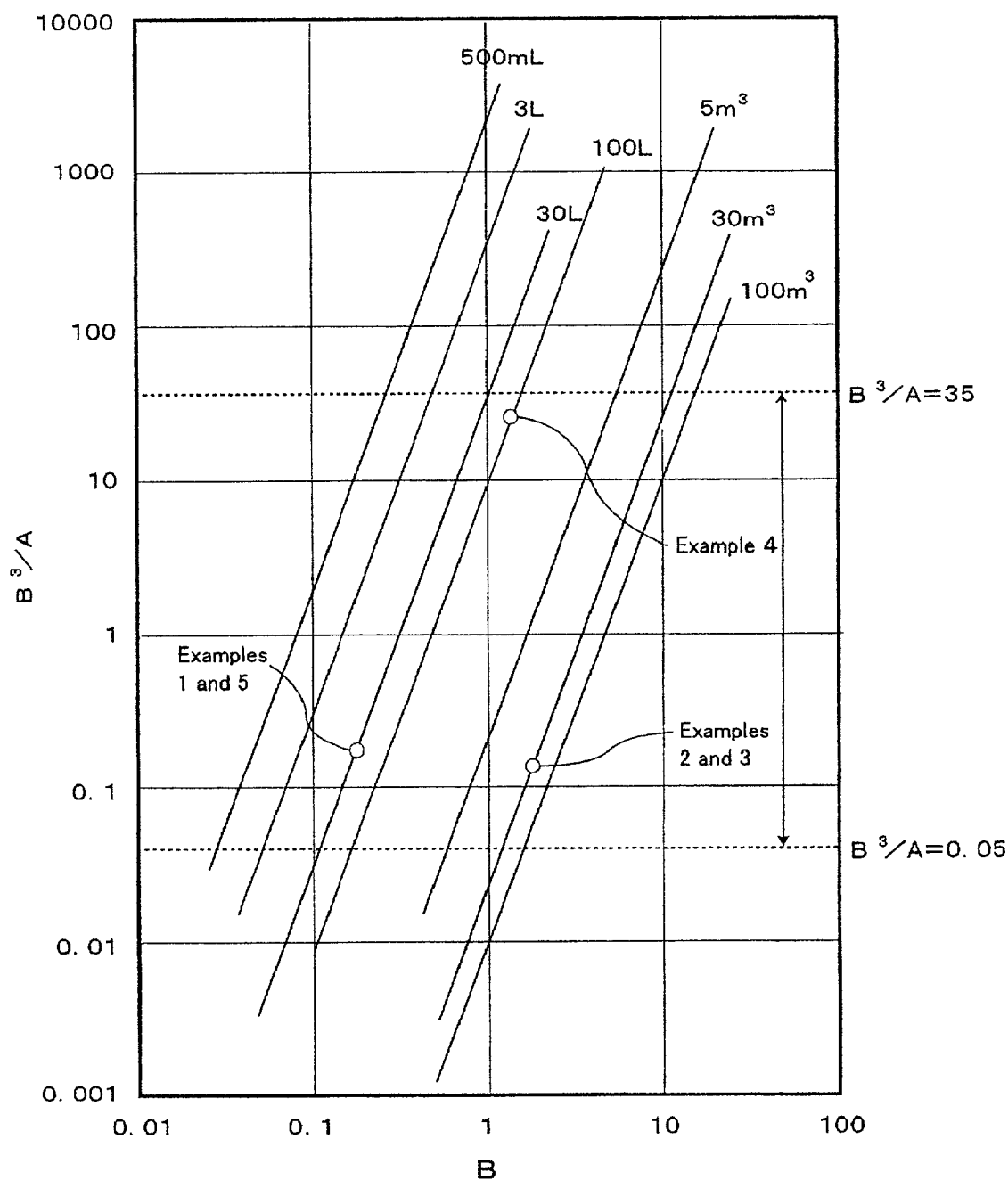
FIG. 3 is a graphic representation of several examples of the relation between the capacity A ($m^3$) of the reaction vessel and the total length B (m) of the connecting pipe on the horizontal basis, each line indicating the relation between B (m) and $B^3/A$ for each constant reaction vessel capacity value A ($m^3$) indicated.

Several examples of the relation between the capacity A (m³) of the above reaction vessel and the total length B (m) of the above connecting pipe on the horizontal basis are graphically shown in FIG. 3. In this graphic representation, each line shows the relation between B (m) and B³/A where a certain value of the reaction vessel capacity A (m³) is indicated. In accordance with the present invention, the values of A (m³) and B (m) are appropriately selected so that the value B³/A may fall within the range defined by the dotted line B³/A=0.05 and the dotted line B³/A=35 as indicated in this graphic representation.

In accordance with the present invention, it is also preferred that the connecting pipe joining the reaction vessel with the condenser has a gradient (θ). By doing so, the liquid retention allowing the formation of a gel-like matter within the connecting pipe can be prevented more reliably. Such a gradient (θ) may be provided from horizontal to upward or from horizontal to downward. For completely preventing the above gel-like matter, even if formed in the connecting pipe, from contaminating the dehydration reaction product in the reaction vessel, the gradient (θ) is preferably directed from the reaction vessel side downward to the condenser side as shown in FIG. 1.

The value of the above gradient (θ) is not particularly restricted but is preferably 0.3 to 70°, considering the disposition of the reaction vessel and condenser and more reliable suppression of the distillate liquid retention, for instance. If it is less than 0.3°, the distillate liquid retention may not be suppressed with high certainty. If it exceeds 70°, it may become difficult to dispose the reaction vessel and condenser easily. The gradient is more preferably 0.5 to 45°, still more preferably 1 to 30°.

In the above-mentioned structure of the dehydration reaction apparatus, it is preferable to reduce areas allowing the distillate liquid retention within the apparatus contacting with the distillate as far as possible so that the distillate liquid retention can be suppressed with more certainty. For example, when the connecting pipe joining the reaction vessel with the condenser is protruding horizontally into the reaction vessel or condenser, liquid retention may possibly occur in the above protruding portion and, therefore, the connecting pipe is preferably disposed so that it will not protrude horizontally into the reaction vessel or condenser. If the connecting site of the connecting pipe with the reaction vessel or condenser and the connecting pipe has a flange and said flange has a void space(s), it is preferable to eliminate the void space(s) of the flange by using a gasket having the same diameter as that of the flange. In this manner, the inside structure of the dehydration reaction apparatus to be used in the practice of the invention is preferably substantially free of any concave parts.

In the above-mentioned structure of the dehydration reaction apparatus, some or all of the connecting pipes joining the reaction vessel with the condenser may be equipped with a heat insulating, warming or heating means. This makes it possible to prevent the vaporized distillate from being condensed on the inside wall of the connecting pipe and efficiently suppress the occurrence of liquid retention within the connecting pipe. As for such means, a double pipe structure may be employed to increase the heat insulating effect, the connecting pipe maybe equipped with a heat insulating material, or a heater or, further, the connecting pipe may be provided with a jacket which enables a heating medium to circulate therein.

In accordance with the present invention, in producing, from a reaction solution, a dehydration reaction product to be applied to a production of a polymer for cement additives, the above dehydration reaction step comprising using a vertical multitubular heat exchanger for exchanging heat between an extratubular fluid and the distillate from the above reaction solution. The dehydration reaction apparatus in the dehydration reaction step comprising using such a vertical multitubular heat exchange also constitutes an embodiment of the present invention. The heat exchanger used as the condenser includes (1) coil-type heat exchanger, (2) double-tubular heat exchanger, (3) multitubular heat exchanger and the like. Among these, "vertical multitubular heat exchanger" in which tubes of the multitubular heat exchanger is used in vertical direction is preferred. The vertical multitubular heat exchanger is constituted, in the dehydration reaction step, as a dehydration reaction apparatus comprising a reaction vessel, a vertical multitubular heat exchanger and a connecting pipe joining the reaction vessel with the vertical multitubular heat exchanger. As for the material of construction and the heat transfer area of the vertical multitubular heat exchanger, the same may be mentioned as mentioned above referring to the condenser.

Figure 6:
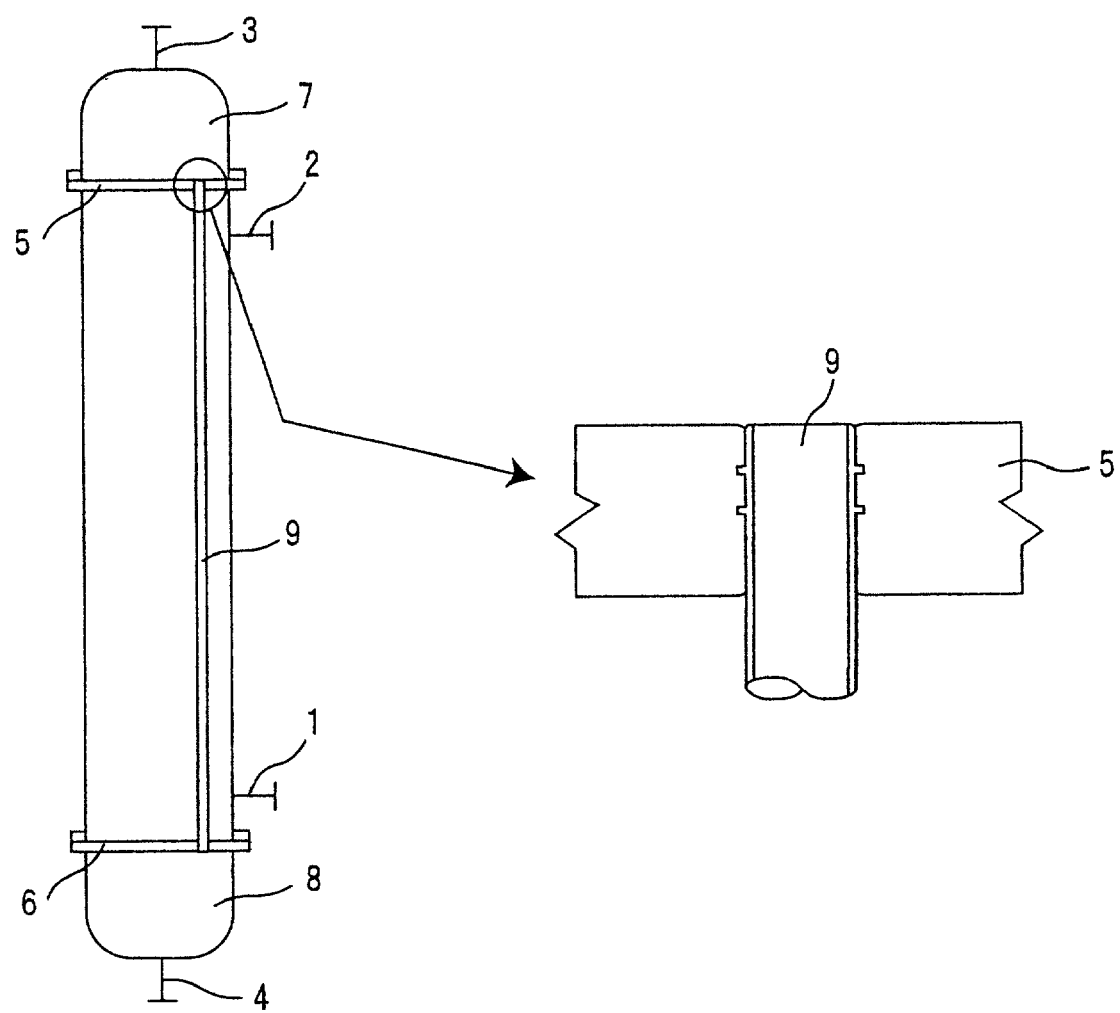
FIG. 6 is a schematic representation of an embodiment of the vertical multitubular heat exchanger to be used in the practice of the invention.
Figure 7:
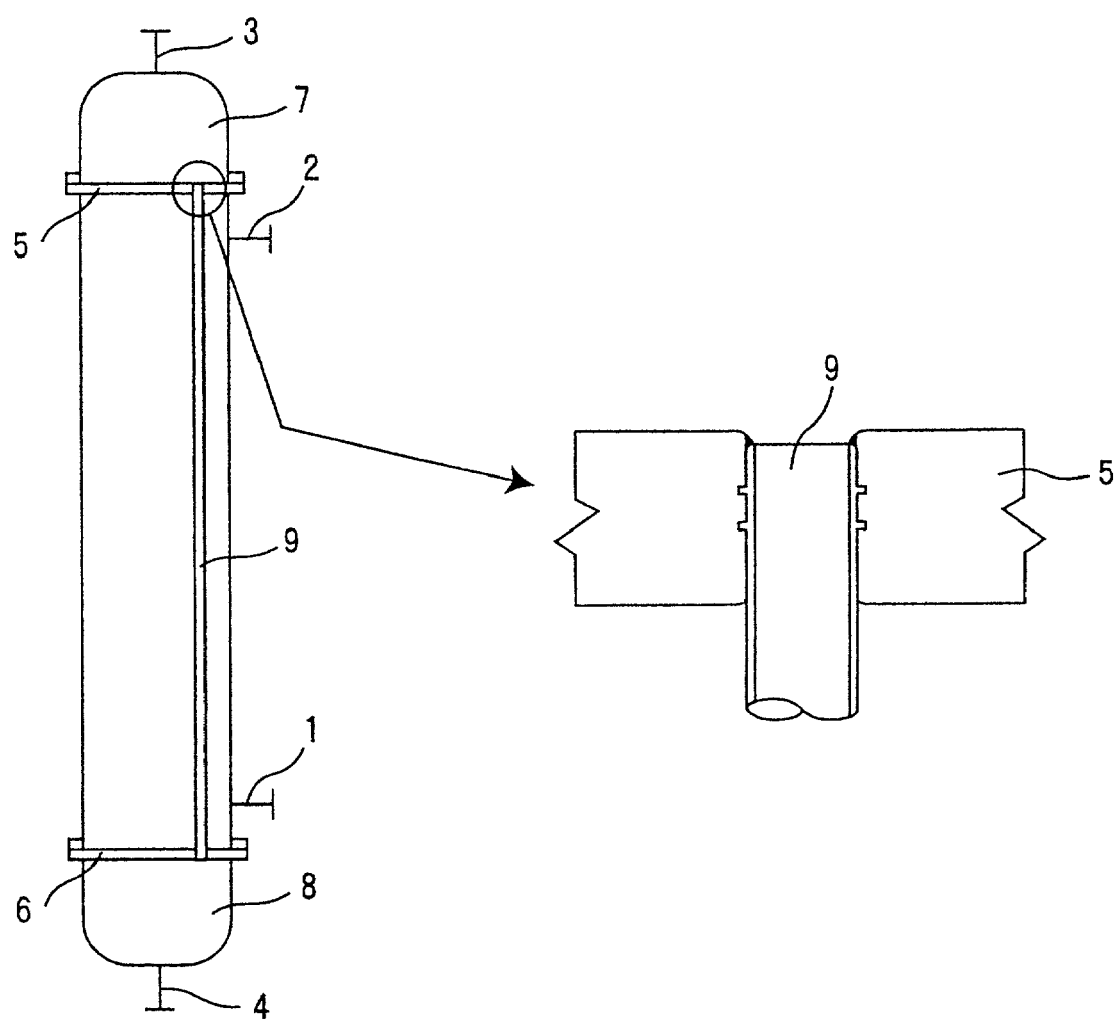
FIG. 7 is a schematic representation of another embodiment of the vertical multitubular heat exchanger to be used in the practice of the invention.
Figure 8:
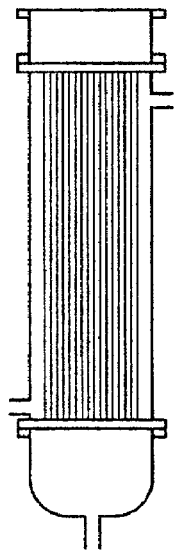
FIG. 8 is a schematic representation for illustrating some examples of the cover of the vertical multitubular heat exchanger to be used in the practice of the invention.
Figure 8:
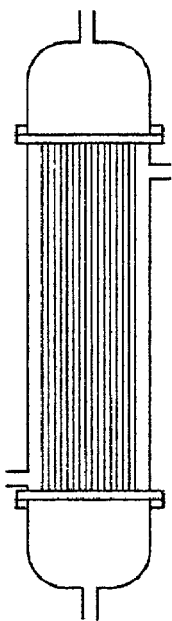
Figure 8:
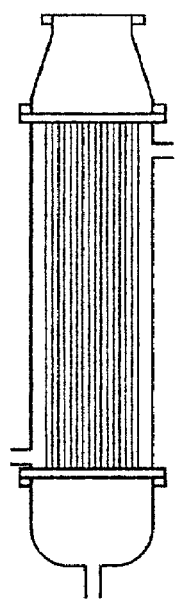
Figure 8:
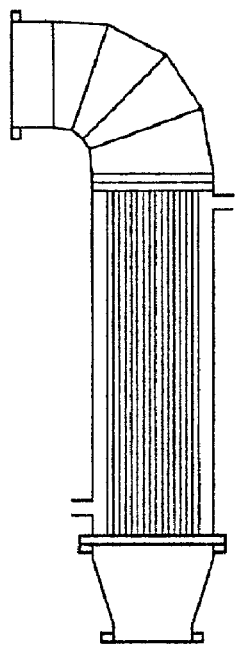
Figure 8:
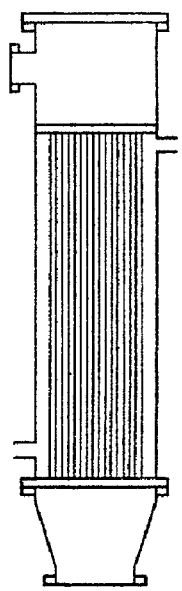
Figure 9:
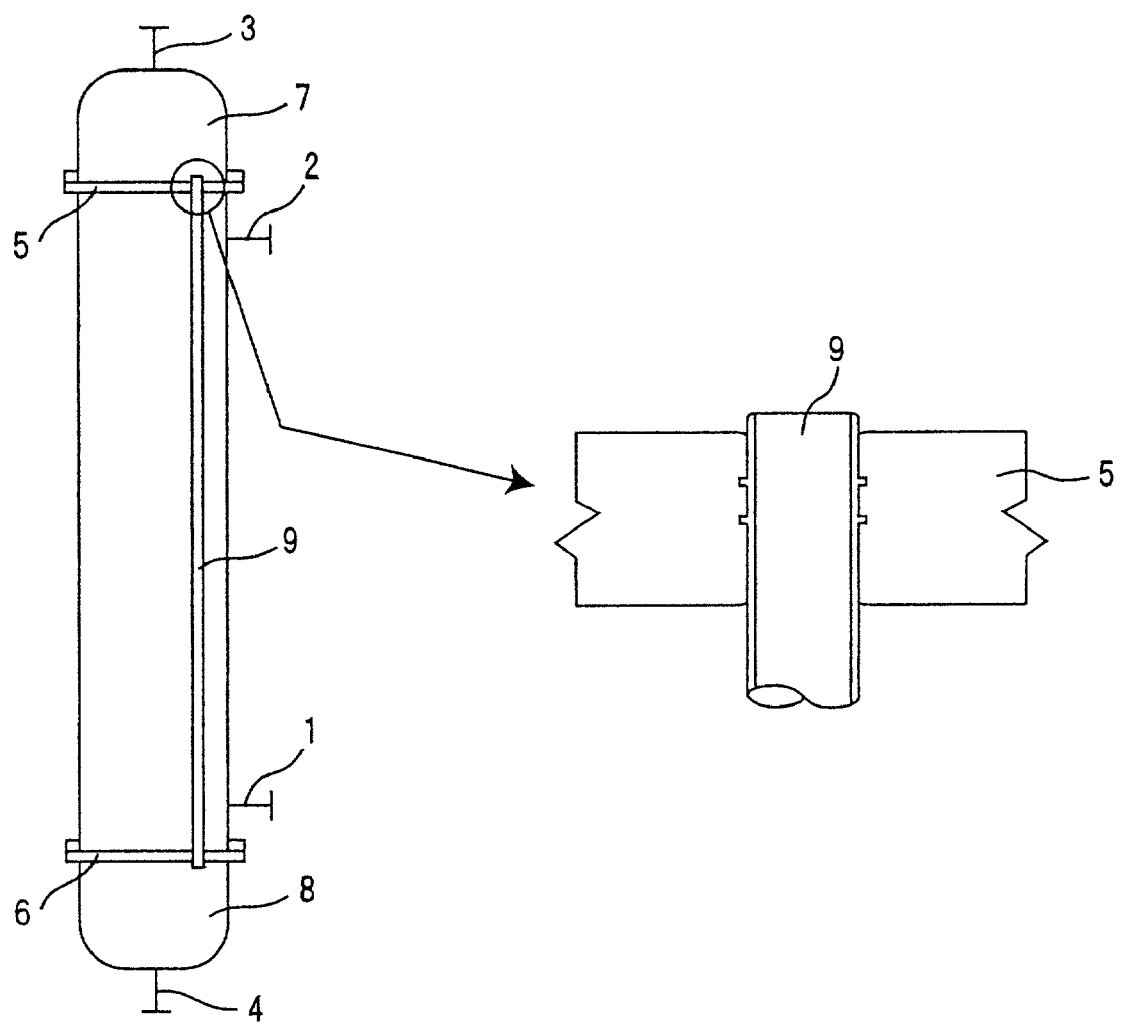
FIG. 9 is a schematic representation of an embodiment of the conventional vertical multitubular heat.

Referring to FIGS. 6 to 8, each schematically illustrating an example of the vertical multitubular heat exchanger to be used in accordance with the invention, the vertical multitubular heat exchanger to be used in the above dehydration reaction apparatus is described in more detail in comparison with FIG. 9 schematically illustrating an example of the conventional vertical multitubular heat exchanger.

In each of FIGS. 6 and 7, the whole of the vertical multitubular heat exchanger to be used in accordance with the present invention is schematically shown in section together with a schematic magnification, in section, of the connecting site between a tubesheet and a heat exchanger tube. In FIG. 8, several vertical multitubular heat exchangers to be used in the practice of the invention are schematically shown in whole section to illustrate several different shapes of the cover. In FIG. 9, the whole of a conventional vertical multitubular heat exchanger is schematically shown in section together with a schematic magnification, in section, of the connecting site between a tubesheet and a heat exchanger tube.

In FIGS. 6, 7 and 9, the whole section of each vertical multitubular heat exchanger is shown on the left and, the section, in magnification, of the connecting site between a tubesheet and a heat exchanger tube is shown on the right. The heat exchanger tube is fitted in the tubesheet by providing several grooves in the tubesheet and expanding the tube. Only one of a plurality of heat exchanger tubes is shown while the others are omitted in the figures. Other parts, such as baffle plates, are also omitted.

The above-mentioned vertical multitubular heat exchanger has a structure comprising a body having an extratubular fluid inlet and an extratubular fluid outlet, covers provided at both upper and lower ends of said body, tubesheets provided in the vicinity of the both upper and lower ends of inside of said body, and a plurality of heat exchanger tubes connected between said tubesheets. As regards the above body, the extratubular fluid inlet is the inlet for introducing a cooling fluid into the vertical multitubular heat exchanger, and the extratubular fluid outlet is the outlet for discharging the cooling fluid out of the vertical multitubular heat exchanger. The mode of storing the extratubular fluid is not restricted to the one-pass type but the two-pass, three-pass and other types may also be employed. Corresponding to this, the shape of the body and the mode of partitioning the body are not particularly restricted, but may be of the longitudinal baffle plate two-pass type, branched flow type, double branched flow type, divided flow type, etc. The size of the body can be appropriately selected according to the size of production and other factors.

As regards the covers, the cover provided at the upper end of the body is also referred to as a top cover, and the cover provided at the bottom of the body as a rear cover. The top cover has an intratubular fluid inlet, and the rear cover has an intratubular fluid outlet. The intratubular fluid inlet is the inlet for introducing the distillate vaporized from the reaction solution into the vertical multitubular heat exchanger, and the intratubular fluid outlet is the outlet for discharging the liquefied and condensed distillate or such distillate partly still vaporized out of the vertical multitubular heat exchanger. As such covers, there may be mentioned such types as illustrated in FIGS. 8(*a*) to (*e*), for instance. Thus, the top cover type may be, for example, the separable cover plate type, integrated cover plate type, or tubesheet-integrated type, or may have, on the upper portion thereof, a bellows-shaped pass for the distillate, as shown in FIG. 8(*d*). The rear cover type may be any of, for example, the fixed tubesheet type, floating head gland type, floating head split flange type or floating head pull-out type.

The positions at which the above tubesheets are to be provided within the body are not particularly restricted as far as they are provided in the vicinity of the both upper and lower ends of inside of the body. The tubesheet provided in the vicinity of the upper end of inside of the body is also referred to as upper tubesheet, and the tubesheet provided in the vicinity of the lower end of inside of the body as lower tubesheet. Such tubesheets separate the extratubular fluid from the intratubular fluid in the vertical multitubular heat exchanger and at the same time fix the heat exchanger tubes within the vertical multitubular heat exchanger.

The outside diameter and length and the number of the above heat exchanger tubes may appropriately selected according to the size and shape of the vertical multitubular heat exchanger and other factors. Generally, steel tubes are used as the heat exchanger tubes and, as for the material thereof, austenitic steel tubes, austenitic-ferritic steel tubes and ferritic steel tubes are preferred since welded steel tubes are easily produced therefrom. When such materials are used, the tubes will not react with compounds in the distillate, hence will not cause degradation of the product and, furthermore, the heat exchanger tubes can be prevented from being corroded.

The above heat exchanger tubes are connected between the tubesheets. For facilitating the connection of the heat exchanger tubes with the tubesheet, it is preferable to perforate the tubesheet and fitting and fixing the heat exchanger tube in the hole to thereby connect the terminal periphery of the heat exchanger tube with the hole provided on the tubesheet. In such a hole, a sealing material may be used for preventing liquid leakage between the terminal periphery of the heat exchanger tube and the hole portion. As for the sealing material, a tape-like matter may be wound around the heat exchanger tube or a packing may be mounted on the hole. The material of such packing is not particularly restricted but may be any of the materials excellent in heat resistance and pressure tightness and inert to the distillate and includes, for example fluorine-containing elastomers and silicones. For providing the heat exchanger tube into the tubesheet without using any sealing material, the tubesheet may be provided with several grooves and the tube may be fit therein by expanding, or by welding. On that occasion, the fitting by welding is preferred since a large number of heat exchanger tubes can be provided in a simple and easy manner and the liquid leakage can be fully prevented.

In accordance with the present invention, there is obtained a configuration that no substantial retention area for the above distillate occurs on the connecting sites between the above tubesheets and the above heat exchanger tubes. If retention areas for the distillate substantially occur, the polymerizable compound contained in the distillate may polymerize to form a gel-like matter since almost no polymerization inhibitor is present in such retentive areas for the distillate while the formation of a gel-like matter is normally inhibited in the reaction solution in which a polymerization inhibitor is generally present. In the vertical multitubular heat exchanger, "connecting site between the tubesheet and the heat exchanger tube" means the site at which the tubesheet is connected with the heat exchanger tube and the vicinity thereof and, when the connection is made by welding, it includes the welding site as well. "Retentive areas for the distillate" means those areas where liquid retention of the liquefied and condensed distillate is formed. That "there are no substantial retentive areas for the distillate" means that the occurrence of retentive areas for the distillate at the connecting sites between the tubesheets and heat exchanger tubes is intentionally prevented, in which areas the polymerizable compound contained in the distillate polymerizes to form a gel-like matter. Thus, it means not only that no retentive areas for the distillate occurs at the connecting sites between the tubesheets and heat exchanger tubes but also that, by intentionally selecting the condition such that retentive areas for the distillate do not occur at the connecting sites, the formation of any gel-like matter at the above connecting sites is inhibited so that no gel-like matter is produced or that the formation of a gel-like matter is inhibited so that the polymers obtainable from the dehydration reaction product can be prevented from being deteriorated in performance characteristics or quality thereof. In the practice of the invention, it is preferred that all of the plurality of heat exchanger tubes has the above configuration. However, some of the heat exchanger tubes may not have the above configuration as long as the effects of the present invention can be manifested.

In accordance with the present invention, it is also possible to take such configuration that no substantial protrusions of the above heat exchanger tubes occurs on the surface, with which the above distillate comes into contact, of at least a tubesheet provided in the vicinity of the upper end out of the above tubesheets. By doing so, it becomes possible to carry out the dehydration reaction step effectively in a manner such that no substantial retentive areas for the distillate occur at the connecting sites between the tubesheet and heat exchanger tubes.

Referring to the above configuration, "at least the tubesheet provided in the vicinity of the upper end out of the tubesheets" means that the upper tubesheet is essential. The upper tubesheet is essential since the distillate tends to stay, at the connecting sites between the upper tubesheet and the heat exchanger tubes to form liquid retention areas. However, by using the upper and lower tubesheets as essential apparatus constituents, it is preferable to prevent the distillate liquid retention with more certainty. "The surface coming into contact with the distillate" is the surface, out of the two surfaces of each tubesheet, which is directed to the cover and thus comes into contact with the distillate and is referred to also as tubesheet surface. That "no substantial protrusions of the heat exchanger tubes occurs on the surface with which the distillate comes into contact" means that the surface coming into contact with the distillate is free of any protrusions of the heat exchanger tubes so that no substantial retentive areas for the distillate can occur at the connecting sites between the tubesheet and heat exchanger tubes, including, for example, the case in which the surface coming into contact with the distillate and the top portion of the heat exchanger tubes are on one and the same plane and the case in which the top portion of the heat exchanger tubes occurs between the surface coming into contact with the distillate and a surface not coming into contact with the distillate, namely between two surfaces of the respective tubesheets. In the latter case, the top portion of each heat exchanger tube is embedded in the tubesheet.

Usable in making the tubesheet surface on which no substantial protrusions of the heat exchanger tubes occur in the above configuration are, for example, the method comprising providing the top portion of the heat exchanger tube in the tubesheet to give one and the same plane therewith and fixing them together by welding, as shown in FIG. 6; the method comprising providing the top portion of the heat exchanger tube in the tubesheet so as to be buried therein, as shown in FIG. 7, fixing the top portion of the heat exchanger tube into a hole of the tubesheet by welding, supplementing a weld material to make the top portion of the weld and the tubesheet surface show one and the same plane, if necessary followed by grinding; and the method comprising first providing the top portion of the heat exchanger so as to protrude from the tubesheet surface, fixing them by welding and then cutting or grinding off the above protruding portion.

In the above configuration, it is preferred that the tubesheet surface is substantially free of concave or convex sites. If the tubesheet has concave or convex sites, the concave sites may possibly serve as retentive areas for the distillate. For making the tubesheet surface substantially free of concave or convex sites when a gap occurs between the tubesheet and the heat exchanger tube or a difference in level occurs between the tubesheet surface and the surface of the top portion of the heat exchanger tube upon embedding the top portion of the heat exchanger tube into the tubesheet, for instance, the concave or convex sites possibly providing retentive areas for the distillate can be eliminated by forming a weld. It is preferred that the tubesheet surface is selected to have the surface roughness value Rmax, standardized in JIS B 0601, of not more than 12.5S, more preferably not more than 3.2S. The retentive areas for the distillate can be eliminated with more certainty thereby. The tubesheet surface roughness can be adjusted to meet the above requirement by connecting each heat exchanger tube with the tubesheet by welding or, further, by surface treatment.

As the method of the above surface treatment, there may be mentioned, for example, mechanical polishing, such as buffing, and electrolytic polishing. Buffing is a method of polishing mainly used to give a smooth surface or gloss surface and can be carried out in the manner of rough grinding using a fixed abrasive, intermediate polishing using a semisolid or unfixed abrasive, or finish polishing. In that case, soft and flexible materials, such as leather and cloth, may be used for polishing and, further, oleaginous or non-oleaginous spraying agents containing rottenstone, chromium oxide, silicon carbide, fused alumina, calcined alumina or the like may also be used for polishing.

Referring to the above-mentioned surface treatment method, electrolytic polishing is a method of polishing used in smoothening the metal surface while melting the same. In cases where the heat exchanger tubes are made of steel, use may be made, for example, of perchloric acid type, sulfuric acid type, phosphoric acid type and sulfuric acid-phosphoric acid type electrolytic polishing solutions. In that case, appropriate polishing solutions will be selected taking into consideration the composition and the extent of heat treatment and modification of the steel since steel species show great differences in structure according thereto. The amount of acetic anhydride generally added to perchloric acid-type electrolytes, as well as the electrolysis temperature, current density, voltage, electrolysis time and other factors can appropriately be selected according to the material of the heat exchanger tubes. It is also possible to subject seamless steel tubes, cold-worked, automatic arc-welded steel tubes, or weld zone finished, automatic arc-welded steel tubes to mechanical polishing and, further to electropolishing treatment.

In the practice of the present invention, it is preferable that the liquefied and condensed distillate be rapidly discharged out of the vertical multitubular heat exchanger since retentive areas for the distillate may be present on the tubesheet surface other than the connecting sites between the tubesheet and heat exchanger tubes. As for the method for attaining such situation, the surface roughness of the tubesheet surface is preferably adjusted in the manner mentioned above, for instance.

The other parts of the vertical multitubular heat exchanger to be used in the practice of the invention are not particularly restricted provided that the above structure is taken. Thus, it may have baffle plates, longitudinal baffle plates, buffer plates, partitioned segment shell flanges, shell cover side flanges, shell side nozzles, floating head covers, fixing rods and spacers, degassing seats, drain discharging seats, gauge seats, supporting legs, hoisting accessories, level gauge seats and so forth, which heat exchangers generally have. Measures against thermal expansion, such as expansion joints, and other measures may also be taken.

In carrying out the production method of a dehydration reaction product according to the present invention, a molecular oxygen-containing gas and/or an antigelling agent may be caused to act on the inside of the dehydration reaction apparatus so that the distillate can more effectively be prevented from being polymerized within the dehydration reaction apparatus. For example, an antigelling agent is preferably added to the distillate in carrying out the dehydration reaction step by exchanging heat between the distillate and an extratubular fluid in the above vertical multitubular heat exchanger. As such antigelling agent, there may be mentioned, for example, polymerization inhibitors, specifically including phenothiazine, tri(p-nitrophenyl)methyl, di(p-fluorophenyl)amine, diphenylpicrylhydrazyl, N-(3-N-oxyanilino-1,3-dimethylbutylidene)aniline oxide, benzoquinone, hydroquinone, methoquinone, butylcatechol, nitrosobenzene, picric acid, dithiobenzoyl disulfide, cupferron, copper(II) chloride and the like. These maybe used singly or two or more of them may be used in combination. Among them, phenothiazine, hydroquinone and methoquinone are preferably used.

The level of addition of the above antigelling agent is preferably selected appropriately according to the dehydration reaction conditions, in particular the quantity of heat to be supplied to the reaction system and the amount of the dehydrating solvent charged into the reaction system, for instance, so that the level of addition may correspond to the amount of the distillate. For example, an addition level of 0.1 to 5,000 ppm by weight relative to the total weight of the starting reactant alcohol or amine and (meth)acrylic acid charged is preferred. If it is less than 0.1 ppm by weight, the effect of the antigelling agent may not be fully manifested. If it exceeds 5,000 ppm by weight, no extra effect corresponding to the amount added can be expected thus, this may possibly be uneconomic. A more preferred level is 5 to 500 ppm by weight.

The method of causing the antigelling agent to act is not particularly restricted provided that the method employed can cause the antigelling agent to effectively produce its effect. For example, the site(s) where it is to be caused to act in the apparatus may be the site(s) acting against the gaseous distillate before being condensed and liquefied in the condenser (vertical multitubular heat exchanger), or the site(s) acting against the liquid distillate after condensed and liquefied in the condenser, or both the sites mentioned above. Since the polymerizable compound in the gaseous distillate is at a high temperature and is not under the action of any antigelling agent, it is particularly effective to cause the antigelling agent to act on the gaseous distillate. As for the timing to be caused to act, it is preferable that it is caused to act successively at a constant level corresponding to the amount of the distillate from the start of distilling off to the end of the reaction so that the total amount may finally fall within the range mentioned above. Furthermore, as the form of the antigelling agent to be caused to act, there may be mentioned the form liquefied (dissolved) using a solvent or the like, the solidified form, such as a powder-like form, the vaporized form, inclusive of a sublimed form, etc. Preferred among them is the form liquefied using a solvent or the like, in particular the form liquefied using the same solvent as the dehydrating solvent.

As the specific method of causing the above antigelling agent to act, there may be mentioned, for example, the method comprising spraying from the upper portion of the condenser, in particular in the vicinity of the column top portion toward the connecting pipe to cause countercurrent contact with the distillate; and the method comprising charging the antigelling agent inside of the condenser and blowing the gaseous distillate thereinto or pouring the liquefied distillate thereinto for contacting, dissolving or dispersing them. In these cases, the antigelling agent may also be caused to act on the joining sites (flange sites) between the reaction vessel and connecting pipe, the flange sites between the connecting pipe and column top portion of the condenser or like flange sites, the protrusion sites at the thermometer or the observation window attached to the reaction vessel, and other sites where a gel-like matter tends to be formed, in addition to the above-mentioned sites of acting. A site near the column top portion of the condenser and/or flange sites are preferably employed as the sites of acting. It is also possible to feed the dehydrating solvent to flange sites to thereby produce the effect of gel formation prevention.

When a dehydration reaction product to be applied to the production of polymers for cement additives is produced from a reaction solution in the production method of a dehydration reaction product according to the present invention, the reaction solution contains (meth)acrylic acid and/or a dehydration reaction product (an ester or amide) derived therefrom. When (meth)acrylic acid and/or a dehydration reaction product (ester or amide) derived therefrom is contained, as in the above case, a gel-like matter is easily formed in the vertical multitubular heat exchanger, so that the effects of the present invention can be fully produced. Thus, in producing a dehydration reaction product to be applied for the production of polymers for cement additives from a reaction solution by the production method of a dehydration reaction product which comprises a dehydration reaction step of using a vertical multitubular heat exchanger for exchanging heat between an extratubular fluid and a distillate from the above reaction mixture, the above reaction mixture preferably contains (meth)acrylic acid and/or a dehydration reaction product derived therefrom.

Further, in the production method of a dehydration reaction product which comprises a dehydration reaction step of subjecting an alcohol and/or an amine with (meth) acrylic acid to esterification and/or amidation in the presence of a dehydrating solvent, the above dehydration reaction is carried out by using a reaction vessel and a water separator as essential apparatus constituents, according to the invention. The water separator to be used in the dehydration reaction apparatus for such dehydration reaction step is described in the following.

The above water separator has any one or a combination of the structure among (1) the structure which is provided with a feeding pipe connected with the above reaction vessel and has a gaseous phase section and a liquid phase section therewithin, said feeding pipe having openings in the gaseous phase section and in the liquid phase section, (2) the structure which is provided with a feeding pipe connected with the above reaction vessel, has a gaseous phase section and a liquid phase section therewithin, has smaller diameter in the lower portion than the diameter in the upper portion and is controlled so that the interface between the dehydrating solvent and the byproduct water may be maintained in the lower portion thereof, and (3) the structure which is provided with a feeding pipe connected with the above reaction vessel and has a gaseous phase section and a liquid phase section therewithin and is provided with a detection device of an interface between the dehydrating solvent and byproduct water and/or a gas/liquid interface and an antigelling agent being caused to act on inside of said detection device. A preferred structure of such a water separator is one in which all the above (1) to (3) are combined.

In the practice of the present invention, the procedure is carried out which comprises, for example, separating the distillate vaporized in the reaction vessel and condensed and liquefied in the condenser into the dehydrating solvent and byproduct water using the above water separator and refluxing the dehydrating solvent to the reaction vessel while removing byproduct water.

In the above structure (1), the feeding pipe has a discharge opening in the gaseous phase section and the liquid phase section. In this case, the liquid distillate is fed to the water separator through that opening in the liquid phase section of the feeding pipe while the gaseous distillate is discharged though the opening in the gaseous phase section, so that the pressure in the liquid phase section of the water separator can be suppressed from changing, whereby the effects of the present invention can effectively be produced.

In the above water separator, the feeding pipe connected with the reaction vessel is a piping for feeding the distillate from the reaction vessel into the water separator. Generally, the reaction vessel is connected with the water separator via the condenser. However, the mode of connection is not particularly restricted provided that the distillate from the reaction vessel can be fed to the water separator. The above feeding pipe may comprise one single pipe or a plurality of pipes and may be branched or not branched. When it is branched, it has a branch pipe, for example, which may be directed from the gaseous phase section to the liquid phase section, or directed from the liquid phase section to the gaseous phase section. Furthermore, the feeding pipe is not particularly restricted in shape of cross section but preferably has a circular section, for instance. Such feeding pipe preferably comprises one single pipe having a shape of circular section (round pipe) and having no branch pipe. The opening is an opening for feeding the distillate fed from the feeding pipe into the water separator and comprises one or a plurality of holes provided at the top or side face of the feeding pipe and/or branch pipe. The shape of such opening is not particularly restricted but preferably is circular, for instance.

In the structure (1) mentioned above, the opening of the feeding pipe in the gaseous phase section preferably comprises one or a plurality of holes made on the side face of said feeding pipe. More preferably, the opening in the gaseous phase section is so contrived that it can discharge the gas alone but cannot discharge the distillate in a liquid form. The opening into the gaseous phase section preferably has a diameter of 1 to 200 mm, more preferably 5 to 100 mm, still more preferably 10 to 50 mm. The number of openings into the gaseous phase section is preferably 1 to 50, more preferably 1 to 10, for instance, although it depends on the size. Thus, it becomes possible to sufficiently suppress the pressure change of the liquid phase section within the water separator.

Further, in the structure (1) mentioned above, the water separator is preferably provided with a baffle plate and the opening of the above feeding pipe in the gaseous phase section is in the direction opposite to the above baffle plate. The baffle plate thus provided makes it possible to divide the liquid phase section in the water separator into a section (A) in which the dehydrating solvent forms the upper phase and byproduct water forms the lower phase and a section (B) in which the dehydrating solvent that has overflowed the baffle plate is present, whereby byproduct water can be removed and the dehydrating solvent can be refluxed efficiently. If, on that occasion, the opening of the feeding pipe in the liquid phase section is in the above section (A) and the opening of the feeding pipe in the gaseous phase section is in the direction opposite to the baffle plate, the distillate discharged from the opening in the gaseous phase section is prevented from entering the above section (B), whereby the byproduct water can be prevented from mixing into the dehydrating solvent to be refluxed.

In the above structure (2), the diameter of the lower portion of the water separator is smaller than the diameter of the upper portion and the interface between the dehydrating solvent and byproduct water is controlled so as to be maintained in the lower portion. These can contribute toward improving the accuracy in detecting the interface between the dehydrating solvent and byproduct water. Therefore, by accurately controlling the amount of the refluxed dehydrating solvent and the amount of byproduct water to be discharged to thereby stably maintain the interface between the dehydrating solvent and byproduct water, it becomes possible to stably carry out the dehydration reaction in the dehydration reaction step. In this case, as the structure that the diameter of the lower portion is smaller than the diameter of the upper portion, the diameter of the lower portion may be reduced as compared with the diameter of the upper portion stepwise or continuously. It is preferred, however, that the diameter of the lower portion be maintained substantially constant and the diameter of the lower portion be made smaller as compared with the diameter of the upper portion, as described later herein referring to the structure shown in FIG. 10. By maintaining the diameter of the lower portion substantially constant, it becomes possible to easily calculating the liquid quantity based on the level of the interface, whereby errors resulting from complex calculations can be eliminated. The interface between the dehydrating solvent and byproduct water can be maintained in the lower portion, for example, by controlling the rate of feeding of the distillate to the water separator and the rate of removing the dehydrating solvent and/or byproduct water separated in the water separator to the out of the water separator while detecting the interface between the dehydrating solvent and byproduct water using a level gauge. On that occasion, it is preferable to adjust the opening extent of the control valve to thereby control the position of the interface.

In the above structure (3), the water separator is provided with a detection device of an interface between the dehydrating solvent and byproduct water and an antigelling agent is caused to act on inside of the above detection device. When the water separator is further provided with a baffle plate and a detection device of an interface between the gaseous phase section and the liquid phase section (dehydrating solvent) in the above section (B), it is preferable to cause an antigelling agent to act on inside of that detection device as well. By causing the antigelling agent to act on inside of the detection device, it becomes possible to fully prevent the detection device inside from being blocked by a gel-like matter and thereby fully prevent occurrence of troubles during production steps and prevent various chemical products from being deteriorated in performance characteristics or quality. The detection device is not particularly restricted provided that it has means for detecting the above-mentioned interface. Thus, for example, there may be mentioned the device having a detection means which utilizes the difference in density or electric resistance and, as mentioned later herein referring to FIG. 1, the so-called level gauge by which the interface is detected by introducing the liquefied distillate from the water separator into a pipe can suitably be used.

The above antigelling agent includes those specifically mentioned hereinabove and the level of addition thereof is also the same as mentioned above.

The method of causing the above antigelling agent to act on the detection device is not particularly restricted provided that the effects of the antigelling agent can be effectively manifested. For example, it is possible to provide the detection device with a nozzle at the site where the agent is caused to act and inject the antigelling agent through the nozzle. The site to be caused to act is preferably in the vicinity of the interface between the dehydrating solvent and byproduct water and/or in the vicinity of the interface between the gaseous phase section and the liquid phase section (dehydrating solvent). The timing to be caused to act is when the dehydrating solvent and/or water is present in the water separator. It is particularly preferable to be caused to act when a polymerizable monomer, such as (meth)acrylic acid is contained within the dehydration solvent or aqueous phase in the water separator, particularly when said monomer is supplied to the water separator, namely during the dehydration for producing a dehydration reaction product and/or during distilling off the dehydrating solvent. The form of the antigelling agent to be caused to act is the same as mentioned hereinabove.

In the practice of the present invention, the material of construction of the water separator and of the feeding pipe and baffle plate to be provided thereto is not particularly restricted but may be any of known materials, for example SUS species, and, from corrosion resistance points of view, preferably SUS 304, SUS 316 or SUS 316L, more preferably SUS 316, SUS 316L or the like. The inside of the water separator may be lined with glass or Teflon for rendering the same inert against corrosiveness of the starting reactants and products.

Figure 10:
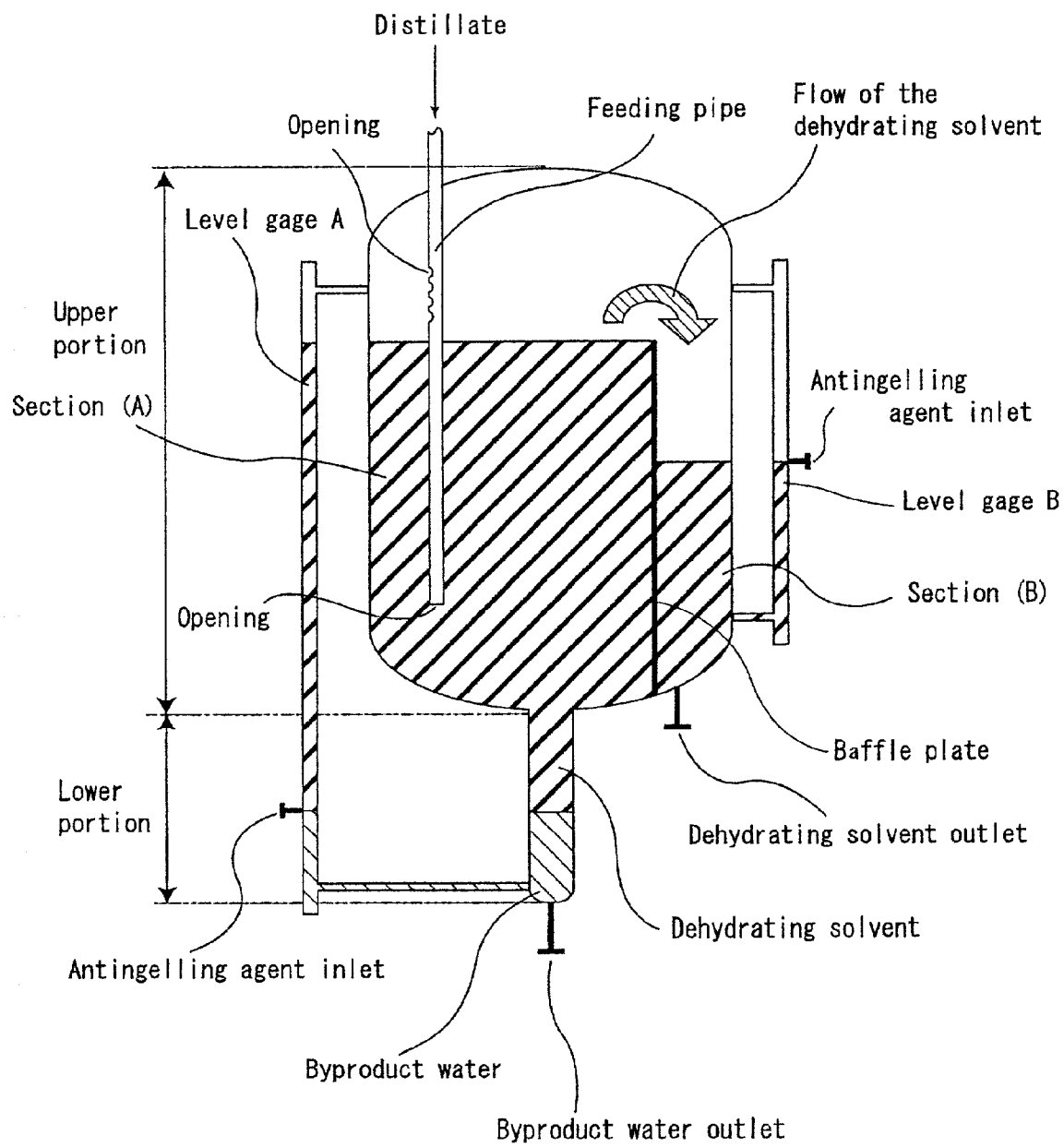
FIG. 10 is a schematic representation of an embodiment of the water separator to be used in the practice of the invention.

Referring to FIG. 10, the water separator to be used in the practice of the present invention is described.

FIG. 10 is a schematic representation of a water separator to be used in the practice of the present invention. In this FIG. 10, an embodiment of the water separator is shown which is constituted in a manner such that it is provided with a feeding pipe and has a gaseous phase section and a liquid phase section therewithin and is further provided with a baffle plate and with a level gauge (A) as a detection device of an interface between the dehydrating agent and byproduct water as well as a level gauge (B) as a detection device of a gas/liquid interface between the gaseous phase section and the liquid phase section (dehydrating solvent) in a section [section (B)] of the water separator on the side opposite to the feeding pipe relative to the baffle plate, together with an outlet for the byproduct water and an outlet for the dehydrating solvent in the lower portion thereof. In this embodiment, an opening of the feeding pipe in the gaseous phase section comprises a plurality of holes made on the side of the feeding pipe in the direction opposite to the baffle plate, a diameter of a lower portion of the water separator is smaller than a diameter of an upper portion, and a piping connected with the byproduct water outlet and the dehydrating solvent outlet is provided with a control valve (not shown) so that the interface between the dehydrating solvent and byproduct water can be maintained in the lower portion by means of the control valve. Further, nozzles (antigelling agent inlets) are provided for causing an antigelling agent to act on the inside of the level gauge (A) and the level gauge (B).

Referring to FIG. 10, the feeding pipe is connected with a condenser (not shown), and the gaseous distillate generated in the reaction vessel is condensed and liquefied in the condenser, passes through the feeding pipe and enters a section [section (A)] in the water separator on the feeding pipe side relative to the baffle plate while, in the section (A), byproduct water is collected in the lower phase and the dehydrating solvent in the upper phase. The dehydrating solvent collected in the upper phase in the section (A) overflows the baffle plate and enters in the section (B) to be collected. The byproduct water collected in the section (A) is discharged through the byproduct water outlet while the interface between the dehydrating solvent and byproduct water is detected by the level gauge (A) and adjusted by means of a control valve so that it may be maintained at a constant level. The dehydrating solvent collected in the section (B) is discharged through the dehydrating solvent outlet and refluxed into the reaction vessel while the interface is detected by the level gauge (B) and adjusted by means of a control valve. On that occasion, the antigelling agent is caused to act on the inside of the level gauge (A) and level gauge (B) and the gauges are prevented from being blocked by gel-like matter formation. In FIG. 10, the dehydrating solvent and byproduct water are indicated by oblique lines.

Referring to FIG. 10, the openings of the feeding pipe in the gaseous phase section and the liquid phase section are preferably located at sites where the distillate discharged from the openings in the gaseous phase section and the liquid phase section can hardly enter into the section (B) or can hardly adhere to the inside wall of the water separator. The baffle plate is preferably provided at sufficiently high position. If the baffle plate is too low, the distillate may overflow the baffle plate and enter the section (B) before it is separated into the dehydrating solvent and byproduct water owing to the difference in density therebetween and the capacity of the water separator cannot be effectively utilized to a satisfactory extent, either.

In the structure shown in FIG. 10, the diameter of the lower portion of the water separator is preferably made sufficiently small as compared with the diameter of the upper portion. For example, the ratio between the diameter of the lower portion and the diameter of the upper portion is preferably 1/20 to 1/2. If the diameter of the lower portion is so small that the ratio becomes less than 1/20, the water-storing capacity becomes small, hence the height must be increases and as a result, the water separator may become excessively large. If diameter of the lower portion is so large that the ratio becomes greater than 1/2, the accuracy in detecting the interface between the dehydrating solvent and byproduct water may not be improved to a satisfactory extent. More preferably, it is 1/10 to 1/3.

In the structure shown in FIG. 10, it is also preferred that the ratio between the height of the lower portion and the height of the upper portion of the water separator is 1/30 to 1/1. If the height of the lower portion is so low that the ratio is less than 1/30, the byproduct water collected in the lower portion may flow into the upper portion, so that the accuracy in detecting the interface between the dehydrating solvent and byproduct water will not be improved to a satisfactory extent. If the height of the lower portion is so high that the ratio is grater than 1/1, the size of the apparatus may become excessively large. A ratio of 1/10 to 1/2 is more preferred.

As mentioned hereinabove, the dehydration reaction apparatus to be used in production the method of a dehydration reaction product according to the present invention makes it possible to prevent the occurrence of liquid retention, which otherwise may lead to the formation of a gel-like matter in the connecting pipe while removing byproduct water from the reaction system, in the production method of a dehydration reaction product which comprises a dehydration reaction step of subjecting a reaction solution containing a polymerizable compound to the dehydration reaction. Thus, the apparatus can realize the effect such that the occurrence of troubles in the production step and the deterioration in performance characteristics or quality of various chemical products are suppressed to a sufficient extent.

As mentioned hereinabove, the vertical multitubular heat exchanger to be used in the production method of a dehydration reaction product according to the present invention can suppress the occurrence, in the vertical multitubular heat exchanger, of liquid retention, which otherwise may lead to the formation of a gel-like matter therein, in producing, from the reaction solution, the dehydration reaction product to be applied to the production of polymers for cement additives. Thus, the heat exchanger can realize the effect such that the occurrence of troubles in the production step and the deterioration in performance characteristics or quality of various chemical products are suppressed to a sufficient extent.

As mentioned hereinabove, the water separator to be used in the production method of a dehydration reaction product according to the present invention can prevent bumping in the reaction vessel and improves and stabilizes the accuracy in detecting the interface between the dehydrating solvent and byproduct water while removing the byproduct water from the reaction system and, further, can satisfactorily prevent the gel-like matter formation in the production method of a dehydration reaction product which comprises a dehydration reaction step of subjecting an alcohol and/or an amine with (meth)acrylic acid to esterification and/or amidation in the presence of a dehydration solvent. Thus, the water separator can realize the effect such that the occurrence of troubles in the production step and the deterioration in performance characteristics or quality of various chemical products are suppressed to a sufficient extent.

In accordance with the present invention, the dehydration reaction step is carried out using any of the above-mentioned forms of the dehydration reaction apparatus. These forms may be used in combination. In the most preferred embodiment, all the above-mentioned forms of the dehydration reaction apparatus are used in combination. These dehydration reaction apparatus, namely the dehydration reaction apparatus to be used in the production method of a dehydration reaction product according to the present invention, also constitute an aspect of the present invention. In preferred embodiments of the present invention, the production method of a dehydration reaction product comprises using these forms of the dehydration reaction apparatus in appropriate combination.

Further, in accordance with the present invention, the dehydration reaction products are preferably used as raw materials for the production of cement additives. Namely, the dehydration reaction products produced by using the method of the present invention are preferably used as raw materials for the production of cement additives. By doing so, it becomes possible to suppress the deterioration in properties or quality of cement additives to be produced and to produce the same stably.

Now, the starting reactants, the method of reaction and the like to be used in the dehydration reaction step according to the present invention are described.

The production method of a dehydration reaction product according to the invention comprises the dehydration reaction step of subjecting a reaction solution containing a polymerizable compound to the dehydration reaction. Such polymerizable compound is, for example, a carboxyl group-containing unsaturated monomer, an amino group-containing unsaturated monomer or a hydroxyl group-containing unsaturated monomer. The carboxyl group-containing unsaturated monomer is a monomer having at least a carboxyl group and an unsaturated bond. More specifically, it includes unsaturated monocarboxylic acids such as (meth)acrylic acid, crotonic acid, tiglic acid, citronellic acid, undecylenic acid, elaidic acid, erucic acid, sorbic acid, linolic acid and the like; unsaturated dicarboxylic acids such as maleic acid, fumaric acid, citraconic acid, mesaconic acid, itaconic acid and the like, and monoesters thereof. These may be used singly or two or more of them may be used in combination.

The above-mentioned dehydration reaction step is preferably a step of subjecting a reaction mixture containing an alcohol and (meth) acrylic acid to esterification reaction to give an ester and/or a step of subjecting a reaction solution containing an amine and (meth)acrylic acid to amidation reaction to give an amide. In these steps, each starting reactant compound may comprise one single species or two or more species. Since these steps easily allow the formation of a gel-like matter, the effects of the present invention can be fully produced. In the present specification, the above-mentioned ester and amide are also referred to as esterification product and amidation product, respectively.

The alcohol to be used in the above esterification reaction is not particularly restricted but may be any hydroxyl group-containing compound, for example an alcohol, a phenol, a diol, an at least trihydric alcohol, or a polyol. Thus, the alcohol includes, for example, primary alcohols such as methanol, ethanol, n-propanol, n-butanol, 2-ethylbutanol, n-octanol, 1-dodecanol, 1-octadecanol, 2-ethylhexanol, cyclohexanol, allyl alcohol and 3-methyl-3-butene-1-ol; secondary alcohols such as isopropyl alcohol, 2-butanol, 2-pentanol, 3-pentanol, 2-heptanol, 3-heptanol, methylamyl alcohol, 2-ocatanol, nonyl alcohol, and $C_{12-14}$ secondary alcohols such as Softanyl (trademark; product of Nippon Shokubai Kagaku); and tertiary alcohols such as tert-butanol and tert-pentanol. The phenol includes phenol, cresol, o-cresol, m-cresol and p-cresol. The diol includes monoethylene glycol, diethylene glycol, triethylene glycol, tetraethylene glycol, polyethylene glycol, monopropylene glycol, dipropylene glycol, polyethylene-polypropylene glycol, diethanolamine and N-butyldiethanolamine. The at least trihydric alcohol or polyol includes glycerol, trimethylolpropane, 1,3,5-pentanetriol, pentaerythritol, glucose, fructose, sorbitol, gluconic acid, tartaric acid and polyvinyl alcohol.

In cases where the dehydration reaction product produced in accordance with the present invention is used as a raw material for the production of polymers for cement additives, the above alcohol preferably contains a compound represented by the general formula (1) given below, and such compound is preferably contained as the main component in the alcohol. In this case, the alcohol may contain or not contain other constituents additionally.

$$R^1O(R^2O)_nH \tag{1}$$

In the formula (1), $R^1$ represents a hydrocarbon group containing 1 to 30 carbon atoms, $R^2O$ are the same or different and each represents an oxyalkylene group containing 2 to 18 carbon atoms, preferably 2 to 8 carbon atoms, and n represents the average number of moles of the oxyalkylene group represented by $R^2O$ as added and is a number of 0 to 300, preferably 2 to 300. The average number of moles added means the average number of moles of the above repeating unit in one mole of the above compound.

If the number of carbon atoms in the above $R^1$ exceeds 30 and/or the number of carbon atoms in the above $R^2O$ exceeds 18, the polymers obtained by using the esterification product as a raw material for the production will be decreased in water solubility. When such polymers are used as cement additives, the performance characteristics for such use, namely the cement dispersing ability and so forth, may become deteriorated. If the above n exceeds 300, the reactivity of the compound represented by the general formula (1) with (meth) acrylic acid may possibly decrease.

As for the number of carbon atoms in the above $R^1$ or $R^2O$, a preferred range is to be selected according to the intended use of the esterification product. For example, when the esterification product is used as a raw material for the production of polymers for cement additives, $R^1$ is, for example, an alkyl group such as methyl, ethyl, n-propyl, isopropyl, n-butyl, tert-butyl, pentyl, hexyl, octyl, nonyl, 2-ethylhexyl, decyl, dodecyl, undecyl, tridecyl, tetradecyl, pentadecyl, hexadecyl, heptadecyl, octadecyl, nonadecyl, eicosyl, heneicosyl or docosyl group; an aryl group such as phenyl group; an alkylphenyl group such as benzyl or nonylphenyl group; a cycloalkyl group such as cyclohexyl group; an alkenyl group; or an alkynyl group. Among these, $C_{1-18}$ straight or branched alkyl groups and aryl groups are preferred, and methyl, ethyl, propyl, butyl and phenyl groups are more preferred.

As the above $R^2O$, there may be mentioned, for example, oxyethylene, oxypropylene, oxybutylene and oxystyrene groups and, among these, oxyethylene, oxypropylene and oxybutylene groups are preferred. $R^2O$ is the repeating unit constituting the compound represented by the general formula (1) and the respective repeating units may be the same or different. In cases where the compound has two or more different repeating unit species, the mode of addition of the respective repeating units is not particularly restricted but may be blockwise or random.

The range of the above-mentioned n is also to be selected according to the intended use of the esterification product. When the esterification product is used as a raw material for the production of polymers for cement additives, for instance, n is preferably 2 to 300, more preferably 5 to 200, still more preferably 8 to 150. When it is used as thickening agents, n is preferably 10 to 250, more preferably 50 to 200.

When the above n is 0, the above $R^1$ is preferably a hydrocarbon group containing not less than 4 carbon atoms from the viewpoint of water solubility and/or boiling point. Thus, when n is 0, the alcohol, in particular methanol or ethanol, has a low boiling point, so that it evaporates together with byproduct water and is dissolved in the byproduct water. Thus, some of the above raw material alcohol is distilled off out of the reaction system, causing a decrease in the yield of the desired esterification product. This needs to be prevented.

The amine to be used in the above amidation reaction is not particularly restricted but may be, for example, ammonia; an aliphatic primary amine such as methylamine, ethylamine, propylamine, butylamine, dodecylamine or cetylamine; an aliphatic secondary amine such as diemthylamine, diethylamine, dipropylamine or diamylamine; an aliphatic tertiary amine such as trimethylamine, triethylamine, tripropylamine or tributylamine; an aliphatic unsaturated amine such as allylamine or diallylamine; an alicyclic amine such as cyclopropylamine, cyclobutylamine or cyclohexylamine; an aromatic monoamine such as aniline, monomethylaniline, dimethylaniline or diphenylaniline; an aromatic diamine such as o-phenylenediamine or m-phenylenediamine; an aminonaphthalene such as α-naphthylamine or β-naphthylamine; a polyalkylenepolyamine such as diethylenetriamine, triethylenetetramine, tetraethylenepentamine, pentaethylenehexamine, dipropylenetriamine, tripropylenetetramine or tetrapropylenepentamine; an oxyethyleneamine such as monoethanolamine, diethanolamine, polyethylene glycol (mono)amine or polyethylene glycol (di)amine; a urea such as urea or thiourea; or a polymer such as polyethyleneimine, polyethyleneimine-ethylene oxide adduct or polyethyleneimine-propylene oxide adduct.

In the above esterification reaction or amidation reaction, a carboxyl group-containing unsaturated monomer other than (meth)acrylic acid can be used therewith. The carboxyl group-containing unsaturated monomer is a monomer having at least a carboxyl group and an unsaturated bond and specifically includes unsaturated monocarboxylic acids such as crotonic acid, tiglic acid, citronellic acid, undecylenic acid, elaidic acid, erucic acid, sorbic acid, linolic acid and the like; and unsaturated dicarboxylic acids such as maleic acid, fumaric acid, citraconic acid, mesaconic acid, itaconic acid and the like. These may be used singly or two or more of them may be used in combination.

The above esterification reaction or amidation reaction may be carried out, if necessary, with a catalyst added to the reaction system. Preferably, the reaction is carried out in the presence of a catalyst. An acid catalyst is particularly suited for use in the esterification reaction and can proceed the reaction swiftly. Such an acid catalyst may also be used in the form of a hydrate and/or an aqueous solution and includes, for example, sulfuric acid, methanesulfonic acid, paratoluenesulfonic acid, paratoluenesulfonic acid hydrate, xylenesulfonic acid, xylenesulfonic acid hydrate, naphthalenesulfonic acid, naphthalenesulfonic acid hydrate, trifluoromethanesulfonic acid, "Nafion (trademark)" resin (product of Du Pont), "Amberlyst 15 (trademark)" resin, phosphotungstic acid, phosphotungstic acid hydrate and hydrochloric acid. These may be used singly or two or more of them may be used in combination.

Among the acid catalysts mentioned above, from the viewpoint of the azeotropic temperature with water and the dehydrating solvent to be mentioned later herein or of the reaction temperature, those having a high boiling point at ordinary pressure (1,013 hPa), more specifically a boiling point at ordinary pressure of not lower than 150° C. are preferred, more preferably not lower than 200° C. As such acid catalysts, there may be mentioned, for example, sulfuric acid (boiling point at ordinary pressure: 317° C.), paratoluenesulfonic acid (boiling point: 185 to 187° C./13.3 Pa (0.1 mmHg)), paratoluenesulfonic acid hydrate and methanesulfonic acid (boiling point: 167° C./1,333.2 Pa (10 mmHg)) and the like. Among them, the use of paratoluenesulfonic acid or paratoluenesulfonic acid hydrate is suitable.

The level of addition of the above acid catalyst is not particularly restricted but may be selected within a range in which the desired catalytic activity can effectively be manifested. A level not more than 0.4 milliequivalent/g, for instance, is preferred. If the addition level exceeds 0.4 milliequivalent/g, the amount of a diester formed in the reaction system by the esterification reaction increases and when such esterification product is used in synthesizing polymers for use as cement additives, the product may show a decreased level of cement dispersing ability. The addition level is more preferably 0.36 to 0.01 milliequivalent/g, still more preferably 0.32 to 0.05 milliequivalent/g. The level of addition of the acid catalyst (milliequivalents/g) is expressed by the value obtainable by dividing the number of equivalents (milliequivalents) of $H^+$ of the acid catalyst used for the reaction by the total amount (g) of the starting reactants charged, more specifically the value calculated by the following formula:

Acid catalyst addition level (milliequivalents/g)=$L/(M+N)$

L: Number of equivalents (milliequivalents) of $H^+$ of the acid catalyst
M: Weight (g) of the alcohol charged
N: Weight (g) of (meth)acrylic acid charged As regards the level of addition of the above acid catalyst, it is also preferred, from the viewpoint of the utility of the esterification product or amidation product to serve as a raw material in the production of polymers to be applied to various uses as chemical products and of the prevention and suppression of the formation of a gel-like matter adversely affecting the dispersing ability and other basic performance characteristics required in such applications, that the weight proportion X (% by weight) of the acid in the acid catalyst relative to the total weight amount of starting reactants and the weight proportion Y (% by weight) of water occurring as the hydrate in the acid catalyst and/or in the form of an aqueous solution satisfy the relation $0<Y<1.81X-1.62$.

The above relation is explained using a specific example. When paratoluenesulfonic acid monohydrate, for instance, is taken as an example, X (% by weight) is the weight proportion of paratoluenesulfonic acid relative to the total weight amount of starting reactants and Y (% by weight) is the weight proportion of the water occurring as the monohydrate relative to the total weight amount of starting reactants. It is to be noted that neither the acid constituent, for example the starting material (meth)acrylic acid, other than the acid catalyst nor such water as byproduct water formed by the esterification reaction can be taken into consideration as the above X and Y.

When the level of addition of the acid catalyst does not satisfy the above relation, for example when Y is 0, water occurring as the hydrate in the acid catalyst and/or in the form of an aqueous solution does not present and the amount of the gel formed in the reaction system during the esterification reaction increases and when such esterification product is used in synthesizing polymers for cement additives, their performance characteristics, for example the cement dispersing ability, may possible be deteriorated. If $Y \geq 1.81X-1.62$, the amount of the gel formed in the reaction system during the esterification reaction increases, leading to the same results as mentioned above. The above acid catalyst may be added to the reaction system all at once or continuously or in portions. From the workability viewpoint, however, it is preferably charged into the reaction vessel all at once together with the starting reactants.

The above esterification reaction and/or amidation reaction is preferably carried out in the presence of a polymerization inhibitor. By doing so, polymerization of the unsaturated carboxylic acid in the starting reactants and the product, namely esterification product and/or amidation product, can be inhibited. As such polymerization inhibitors, those known in the art can be used without any particular limitation. Fro example, there maybe mentioned phenothiazine, tri(p-nitrophenyl)methyl, di(p-fluorophenyl)amine, diphenylpicrylhydrazyl, N-(3-N-oxyanilino-1,3-dimethylbutylidene)aniline oxide, benzoquinone, hydroquinone, methoquinone, butylcatechol, nitrosobenzene, picric acid, dithiobenzoyl disulfide, cupferron, copper(II) chloride, etc. These may be used singly or two or more of them may be used in combination. Among these, phenothiazine, hydroquinone and methoquinone are preferably used in view of their solubility. These can show their polymerization inhibiting ability very effectively in the dehydration reaction step as well in the step of distilling off the solvent, hence are very useful.

The level of addition of the above polymerization inhibitor is preferably 0.001 to 1% by weight with the total amount of the starting reactants, namely alcohol, amine and acid, being taken as 100% by weight. If it is less than 0.001% by weight, the polymerization inhibiting effect will be manifested only to an unsatisfactory extent, hence it will become difficult to effectively inhibit the polymerization of the starting reactant and/or product. If it exceeds 1% by weight, the amount of the polymerization inhibitor remaining in the esterification product increases, which may possibly deteriorate the quality and performance characteristics. Further, the excessive portion added will not produce any extra effect, which may be disadvantageous from the economical viewpoint. A level of 0.001 to 0.1% by weight is more preferred.

The dehydration reaction procedure in the above esterification and/or amidation reaction may be carried out without using any dehydrating solvent but is preferably carried out using a dehydration solvent while, for example, distilling byproduct water off out of the reaction system azeotropically together with the dehydrating solvent, condensing and liquefying the azeotrope, separating and removing byproduct water and refluxing the dehydrating solvent. By doing so, byproduct water formed by the esterification and/or amidation reaction can be efficiently removed azeotropically. Such dehydrating agent is not particularly restricted but may be any solvent capable of forming an azeotrope with water. Thus, it includes, for example, benzene, toluene, xylene, cyclohexane, dioxane, pentane, hexane, heptane, chlorobenzene and isopropyl ether. These may be used singly or two or more of them may be used in combination. Among these, those having an azeotropic temperature with water of not higher than 150° C. are preferred and those having an azeotropic temperature of 60 to 90° C. are more preferred. As such dehydrating solvents, there may specifically be mentioned cyclohexane, toluene, dioxane, benzene, isopropyl ether, hexane, heptane and the like. When the azeotropic temperature with water exceeds 150° C., the workability, inclusive of the controllability of the temperature in the reaction system during reaction and the controllability in the condensation/liquefaction treatment of the distillate, may possibly become poor.

In the dehydration reaction procedure using the above dehydrating solvent, the dehydrating solvent is used preferably in an amount of 0 to 100% by weight with the total charged amount of the starting reactants, namely alcohol, amine and acid, being taken as 100% by weight. When the amount exceeds 100% by weight, the addition in excess will not produce any extra effect and, in addition, an increased amount of heat is required to maintain the reaction temperature at a constant level, which may possibly be disadvantage in economical viewpoint. An amount of 2 to 50% by weight is more preferred.

In the above dehydration reaction step, the esterification or amidation reaction can be carried out by any of the batchwise and continuous reaction procedures. The batchwise procedure is preferred, however. The reaction conditions are not particularly restricted but those conditions under which the reaction can proceed smoothly. For example, the reaction temperature is preferably 30 to 180° C., more preferably 60 to 130° C., still more preferably 90 to 125° C., most preferably 100 to 120° C. If it is lower than 30° C., the refluxing of the dehydrating solvent will be slow and a longer time will be required for dehydration and, in addition, the reaction may not proceed smoothly. If it is higher than 180° C., some of the starting reactants may decompose, hence the polymers obtainable from the esterification or amidation reaction product may be deteriorated in dispersing and thickening characteristics in various uses, for example cement dispersing ability, polymerization of the starting reactants or contamination of the distillate with the starting reactants may increase or the esterification or amidation product may possibly be deteriorated in performance characteristics or quality.

Under the above reaction conditions, the reaction time is preferably such that the conversion of not lower than 70% is attained, as mentioned later herein, more preferably not lower than 80%, still more preferably not lower than 98%. Normally, it is 1 to 100 hours, preferably 3 to 60 hours. As for the reaction pressure, the reaction may be carried out at ordinary pressure or under reduced pressure. From the equipment viewpoint, the reaction is preferably carried out at ordinary pressure, however.

Preferably, the above esterification or amidation reaction is carried out until a conversion of not lower than 70% is attained. If it is less than 70%, the yield of the product ester or amide will be unsatisfactory and, in addition, the polymers for cement additives obtainable by using such product as a raw material for polymerization may possibly be deteriorated in performance characteristics required for the intended uses, namely the cement dispersing ability and so on. More preferably, it is 70 to 99%, still more preferably 80 to 98%. The above conversion is the ratio between the amount of the starting reactant alcohol or amine as charged and the amount thereof at the time of completion of the reaction and is, for example, the value (%) calculated using the formula given below, following determination of respective peak areas by liquid chromatography (LC) under the conditions shown below:

Esterification percentage (%)=[(S−T)/S]×100

S: Area measured for the alcohol charged
T: Area measured for the alcohol after completion of the esterification Conversion Measuring Conditions
Analysis apparatus: Waters Millennium Chromatography Manager (trademark)
Detector: Waters 410 RI detector (trademark)
Column to be used: GL Science Inertsil ODS-2 (inside diameter 4.6 mm, length 250 mm) (trademark), three columns Column temperature: 40° C.
Eluent: A solution prepared by mixing 8,946 g of water, 6,000 g of acetonitrile and 54 g of acetic acid and adjusting the pH to 4.0 with a 30% aqueous solution of sodium hydroxide.

Flow rate: 0.6 ml/min.

When an acid catalyst is used in the dehydration reaction step in carrying out the production method of a dehydration reaction product according to the present invention, it is preferable to carry out a neutralization step for neutralizing the acid catalyst and (meth)acrylic acid. By doing so, the catalyst loses its activity and the dehydration reaction product obtained by the esterification or amidation reaction can be prevented from being hydrolyzed and the formation of impurities not to be involved in polymerization can be suppressed and, as a result, the polymers can be suppressed from being deteriorated in quality or performance characteristics. When a dehydrating solvent is used, it is preferable to carry out a step of removing solvent by distillation for distilling off the above dehydrating solvent.

The above neutralization step is preferably carried out, for example, by neutralizing the acid catalyst with a neutralizing agent after completion of the esterification or amidation reaction.

The above neutralizing agent is not particularly restricted but may be any agent capable of neutralizing the acid catalyst. Thus, there may be mentioned, for example, alkali metal or alkaline earth metal hydroxides such as sodium hydroxide, potassium hydroxide, calcium hydroxide and lithium hydroxide; alkali metal or alkaline earth metal carbonates such as sodium carbonate, calcium carbonate and lithium carbonate; ammonia and amines such as monoethanolamine, diethanolamine and triethanolamine. These may be used singly or in combination of two or more. The form of the neutralizing agent is not particularly restricted and, for example, the form of an alkaline aqueous solution is preferred.

In the above neutralization step, the acid catalyst and (meth)acrylic acid are neutralized and it is preferred that the amount of the neutralizing agent be selected so that the whole amount of the acid catalysts and some of (meth)acrylic acid can be neutralized. In this case, the portion of (meth)acrylic acid to be neutralized is preferably not more than 20% by weight, more preferably 0.01 to 5% by weight with the amount of (meth)acrylic acid remaining after the esterification or amidation reaction being taken as 100% by weight. Among the acid catalyst and (meth)acrylic acid, the acid catalyst is higher in acid strength, hence the acid catalyst is first neutralized.

As regards the method of neutralization in the above neutralization step, when the esterification or amidation reaction is carried out in a dehydrating solvent, it is preferable to add a large amount of water to the reaction system together with the alkali. This is because, in the absence of a large amount of water, the alkali, which is hardly soluble in the dehydrating solvent, floats in a concentrated state in the reaction system and such floating of the high concentration alkali continues for a long period until the alkali has been consumed for neutralization, thus causing hydrolysis of the esterification or amidation product. In this case, the amount of addition of water may vary depending on the application form of the alkali but, when a 40 to 60% by weight of an alkaline aqueous solution is used as the neutralizing agent, for example, water is preferably added, in addition to the alkali aqueous solution, generally in an amount of 5 to 1,000 parts by weight, more preferably 10 to 100 parts by weight, per part by weight of the alkali aqueous solution. If the amount of water is less than 5 parts by weight, the alkali may be unhomogeneous in the reaction system. If it exceeds 1,000 parts by weight, a separate neutralization vessel may be required to secure the productivity, leading to an increase in production cost.

The neutralization temperature in the above neutralization step is preferably not higher than 90° C., for instance, more preferably 0 to 80° C., still more preferably 25 to 65° C. At temperatures higher than 90° C., the neutralizing agent added may act as a hydrolyzing catalyst, possibly causing hydrolyzate formation in large amounts. At not higher than 80° C., hydrolyzates formation is sufficiently inhibited whereas, at lower than 0° C., the reaction mixture becomes viscous and the stirring becomes difficult accordingly and, in addition, a long period of time is required for increasing the temperature to a predetermined temperature for the removal of water by distillation after the reaction and/or it becomes necessary to provide a new cooling means (apparatus) for lowering the temperature below room temperature, whereby the production cost may possibly be increased.

The method of distilling off the dehydrating solvent in the above-mentioned solvent removing step is not particularly restricted. For example, the dehydrating solvent alone may be distilled off, or the solvent may be distilled off with an appropriate additive added. It is preferable, however, to use water and distill off the dehydrating solvent azeotropically. In this case, no substantial amount of the acid catalyst or alkali remains in the reaction system owing to the neutralization step being carried out, so that even when water is added and the temperature is raised, no hydrolysis reaction takes place. By using such a method, the dehydrating solvent can be removed efficiently at lower temperatures.

The conditions for the above method of distilling off are not particularly restricted provided that the dehydrating solvent in the reaction system can appropriately be distilled off (evaporated). Generally, when water is used, the liquid temperature (at ordinary pressure) in the reaction vessel during distilling off the solvent, for instance, is preferably 80 to 120° C., more preferably 90 to 110° C. When water is not used, a temperature of 80 to 160° C. is generally preferred and a temperature of 90 to 150° C. is more preferred. In both of the above cases, a lower temperature than the above-specified range may fail to be a sufficient temperature (sufficient quantity of heat) to evaporate the dehydrating solvent while, at a higher temperature than the above range, polymerization may be caused and a large quantity of heat may be consumed in evaporating a large amount of low-boiling-point starting materials. As for the pressure within the reaction vessel, the distillation may be carried out at ordinary pressure or under reduced pressure. From the equipment viewpoint, however, it is preferably carried out at ordinary pressure.

The apparatus system used in the dehydration reaction step is preferably used as the apparatus system in the above step of distilling off the solvent.

The dehydration reaction product obtainable by the production method of a dehydration reaction product according to the present invention can suitably be applied as a raw material for the production of various polymers, namely polymers to be used as such chemical products as cement additives, pigment dispersants for dispersing calcium carbonate, carbon black, ink and the like, scaling inhibitors, dispersants for gypsum-water slurries, dispersants for coal-water slurries (CWM) and thickening agents.

In the following, a method of producing polymers for cement dispersants using, as a raw material, the dehydration reaction product obtainable by the production method of a dehydration reaction product, a method of producing cement additives containing said polymers for cement dispersants and a method of using said cement additives are described.

As the above polymers for cement dispersants, there may be mentioned polycarboxylic acid type polymers obtainable by polymerizing a monomer comprising the dehydration reaction product obtained and an unsaturated carboxylic acid monomer. The polymerization method of such polycarboxylic acid type polymer is not particularly restricted but any of those known polymerization methods such as solution polymerization or bulk polymerization, for instance, using a polymerization initiator may be employed.

The above unsaturated carboxylic acid monomer includes, for example, unsaturated monocarboxylic acids such as (meth)acrylic acid, crotonic acid, tiglic acid, citronellic acid, undecylenic acid, elaidic acid, erucic acid, sorbic acid, linolic acid and the like; unsaturated dicarboxylic acids such as maleic acid, fumaric acid, citraconic acid, mesaconic acid, itaconic acid and the like; and monoesters derived from these dicarboxylic acids and alcohols; as well as univalent metal salts, bivalent metal salts, ammonium salts and organic amine salts derived therefrom.

The polycarboxylic acid type polymers may also be copolymerized with a monomer(s) other than the unsaturated carboxylic acid monomers, if necessary. As such monomers, there may be mentioned, unsaturated amides such as (meth)acrylamide and (meth)acrylalkylamides; vinyl esters such as vinyl acetate and vinyl propionate; unsaturated sulfonic acids such as vinylsulfonic acid, (meth) allylsulfonic acid, sulfoethyl (meth) acrylate, 2-methylpropanesulfonic acid (meth) acrylamide and styrenesulfonic acid, and univalent metal salts, bivalent metal salts, ammonium salts and organic amine salts thereof; aromatic vinyls such as styrene and α-methylstyrene; esters of (meth)acrylic acid with $C_{1-18}$, preferably $C_{1-15}$, aliphatic alcohols or phenyl group-containing alcohols such as benzyl alcohol; polyalkylene glycol mono(meth)acrylates; polyalkylene glycol mono (meth)allyl ethers; and so forth.

The above polycarboxylic acid type polymers are preferably polymers having a weight average molecular weight within a specific range. For example, the weight average molecular weight on the polyethylene glycol equivalent basis as determined by gel permeation chromatography (hereinafter, "GPC") under the measuring conditions given below is preferably 500 to 500,000. If it is less than 500, the water reducing capacity of the cement additives may decrease. If it exceeds 500,000, the water reducing capacity and slump loss preventing effects of the cement additives may decrease. A range of 5,000 to 300,000 is more preferred and a range of 8,000 to 100,000 is still more preferred.

The above GPC is constituted of an eluent storage tank, eluent feeding apparatus, automated sampler, column oven, column, detector, data processing machine and so forth. The molecular weight can be determined, for example by combinedly using the following commercial devices and selecting the measuring conditions:

Molecular Weight Measuring Conditions

Model: LC Module 1 plus (trademark; product of Waters)
    Detector: Differential refractometer (RI) 410 (trademark; product of Waters)
Eluent: A solution of 0.05 M sodium acetate in an acetonitrile/ion-exchange water (40/60) mixture as adjusted to pH 6 with acetic acid is used.
Eluent flow rate: 1.0 ml/min.

Columns:
TSK-GEL guard column (inside diameter 6 mm, length 40 mm) +
TSK-GEL G-4000 SWXL (inside diameter 7.8 mm, length 300 mm) +
TSK-GEL G-3000 SWXL (inside diameter 7.8 mm, length 300 mm) +
TSK-GEL G-2000 SWXL (inside diameter 7.8 mm, length 300 mm)
(all being trademarks; products of Tosoh Corp.)
Column oven temperature: 40° C.

Working curve: The working curve varies according to the number of standard samples and the molecular weights thereof, the method of baseline drawing, the method of obtaining an approximate expression for the working curve and the like. Therefore, the following conditions are preferably established.

1. Standard Samples

Commercially available standard polyethylene oxide (PEO) and standard polyethylene glycol (PEG) are used as the standard samples. Preferably, the species having the following molecular weights are used as the standard samples: 1470, 4250, 7100, 12600, 24000, 46000, 85000, 219300, 272500 (9 points in total).

In selecting these standard samples, the following were taken into consideration:

(1) at least 7 standard samples having a molecular weight not less than 900 are included;
(2) at least one standard sample having a molecular weight between 900 and 2,000 is included;
(3) at least 3 standard samples having a molecular weight between 2,000 and 60,000 are included;
(4) at least one standard sample having a molecular weight of 200,000±30,000 is included; and
(5) at least one standard sample having a molecular weight of 270,000±30,000 is included.

2. Method of Baseline Drawing

Upper limit to molecular weight: A point where a peak appears from a horizontal and stable baseline.

Lower limit to molecular weight: A point where the main peak detection is finished.

3. Approximate Expression of the Working Curve

Based on the working curve ("elution time" versus "logarithm of molecular weight") constructed by using the above standard samples, a cubic approximate expression is derived and this is used in calculations.

The cement dispersants comprising the above-mentioned polycarboxylic acid type polymer can show good cement dispersing and slump maintaining capacities. If necessary, however, any of known cement additives (cement dispersants) other than the polycarboxylic acid type polymer may further be incorporated therein.

In the above cement dispersant compositions, there may also be incorporated of air entraining agents, cement wetting agents, expanding agents, water-proofing agents, retarders, quick setting agents, water-soluble high-molecular substances, thickening agents, flocculants, drying shrinkage reducing agents, reinforcing agents, accelerators, antifoaming agents and so forth.

The thus-obtained cement dispersants are used in cement compositions comprising cement and water, for example in hydraulic cements such as portland cement, high belite content cement, alumina cement or any of various cement blends, and in other hydraulic materials than cements such as gypsum.

The above cement dispersants produce excellent effects even at lower addition levels into hydraulic materials as compared with the conventional cement dispersants. In adding to mortar or concrete in which hydraulic cement is used, for instance, they may be added, in the step of blending, in an amount of 0.001 to 5% by weight relative to 100% by weight of cement. At a level lower than 0.001% by weight, effects of the cement dispersant may not be fully produced. If the level exceeds 5% by weight, no more substantial increase in effect will be obtained, which maybe disadvantage in an economical viewpoint. A level of 0.01 to 1% by weight is more preferred. Thereby, various effects can be produced, for example attainment of high water reducing percentage, improvements in slump loss preventing ability, reductions in water content per unit volume of concrete, increases in strength and improvements in durability.

The production method of a dehydration reaction product according to the invention, which has the constitution mentioned above, can satisfactorily prevent the occurrence of troubles in the production process and the deterioration in performance or quality of various chemical products and thus can give high-quality dehydration reaction products. Such dehydration reaction products can be used as raw materials in the production of cement additives (cement dispersants), dispersants for pigments such as calcium carbonate, carbon black, ink and the like, scaling inhibitors, dispersants for gypsum-water slurries, dispersants for coal-water slurries (CWM), thickeners and other chemical products.

PREFERRED EMBODIMENTS OF THE INVENTION

Figure 4:
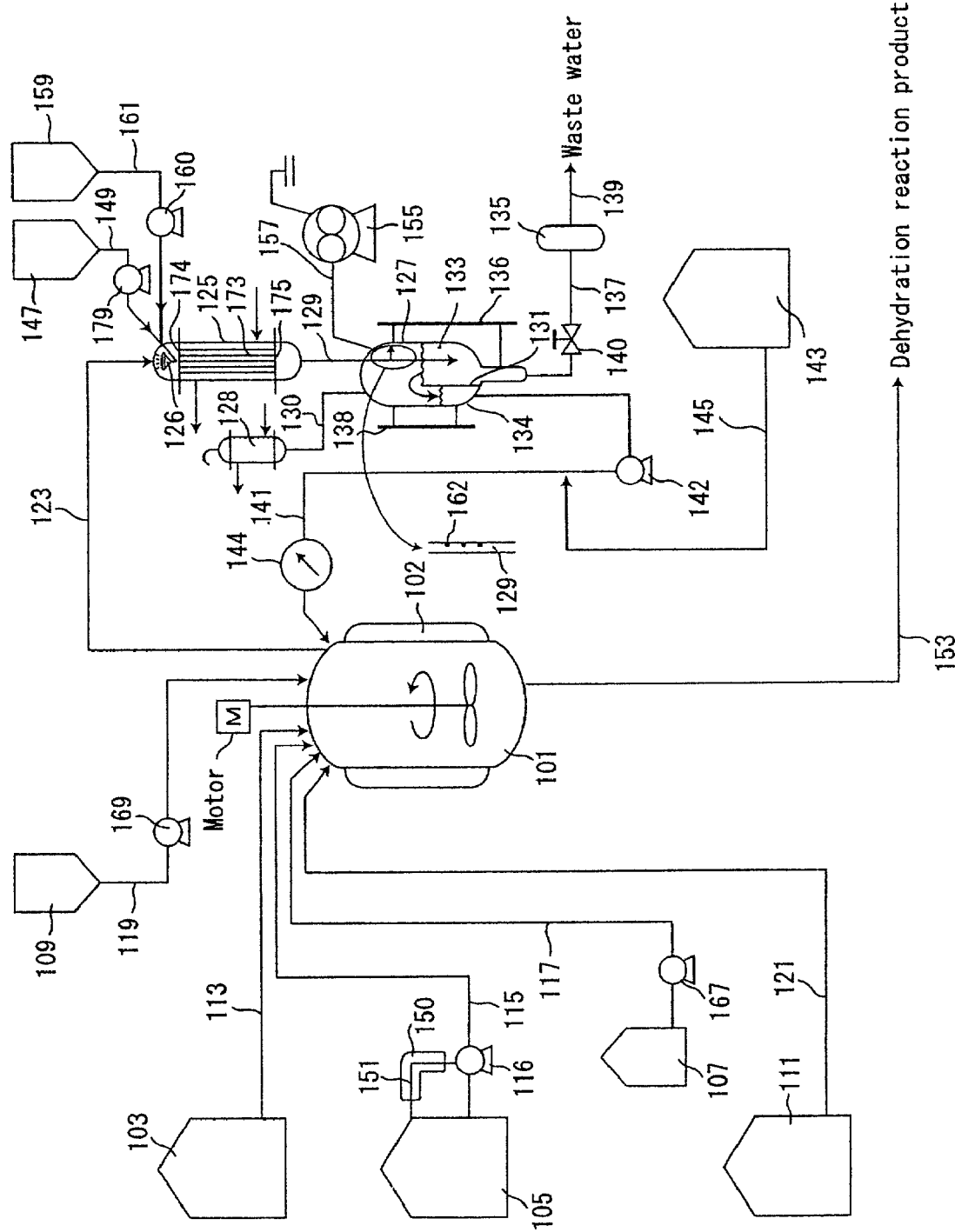
FIG. 4 is a schematic representation of an embodiment of the apparatus constitution to be used in the production method of a dehydration reaction product according to the invention.

The production method of a dehydration reaction product according to the present invention and the dehydration reaction apparatus to be used therefor are now described referring to FIG. 4, which schematically illustrates an embodiment of the apparatus constitution. Such embodiment includes all the configurations mentioned above and is a typical example of the present invention but, however, it is by no means limitative of the embodiment of the present invention.

FIG. 4 shows an apparatus constitution for carrying out the dehydration reaction step raising the temperature to a predetermined level, the neutralization step after lowering the temperature to a predetermined level and, then, the step of distilling off the dehydrating solvent after raising the temperature to a predetermined level. In such apparatus constitution, a recycling system is formed in which a distillate containing byproduct water formed by the dehydration reaction in a reaction vessel 101 is allowed to distill out, the distillate is condensed and liquefied in a condenser 125 while preventing the formation of a gel-like matter, byproduct water is separated and removed in a water separator 127 and the remaining distillate is returned, by means of a pump 142, to the reaction vessel 101 at a predetermined solvent circulation rate. In such recycling system, the upper portion of the reaction vessel 101 is connected, via a connecting pipe 123, with the column top portion of a vertical multitubular heat exchanger (condenser) 125 of the concurrent or countercurrent contact type and the bottom portion of the condenser 125 and the upper portion of the water separator 127 are connected together via piping 129, so that the reaction vessel 101 is connected with the water separator 127 via the feeding pipe 129.

In the following, the case in which the dehydration reaction is an esterification reaction is described.

The reaction vessel 101 is provided with an external jacket 102 as a heat exchanging means, in which hot water or steam under pressure can be used as a heating medium.

Within the above reaction vessel 101, there are disposed temperature sensors (not shown) for measuring the reaction temperature at several appropriate sites. Such temperature sensors are electrically connected with a main controller (not shown) so that the reaction temperature may be maintained at a predetermined level. As the above apparatus system, there may be mentioned, for example, the jacket 102 and the like provided to the reaction vessel 101.

In the above embodiment, the dehydration reaction apparatus, which is constituted of the reaction vessel 101 and the condenser 125 and equipped with the connecting pipe 123 joining the reaction vessel 101 with the condenser 125, satisfies the requirement:

$$0.05 < (B^3/A) < 35$$

where A ($m^3$) is a capacity of the reaction vessel 101 and B is a total length (m), on the horizontal basis, of the connecting pipe 123. Thereby, the effects of the present invention can be produced while suppressing the gel-like matter formation in the connecting pipe 123 and the like. Further, when the capacity A ($m^3$) of the reaction vessel 101 is selected within the range of 0.1 to 100 $m^3$ or a gradient ($\theta$) is given to the connecting pipe 123 or said gradient is selected within the range of 0.3 to 70°, the gel-like matter formation can be inhibited more effectively.

The above condenser 125 is made of SUS 304 and constituted of a body and covers and, an upper tubesheet 174 and a lower tubesheet 175 are provided in the vicinity of both the upper and lower ends of inside of the body respectively and a plurality of heat exchanger tubes 173 are connected between the above tubesheets. The body has an extratubular fluid inlet and an extratubular fluid outlet and the arrows shown indicate that an extratubular fluid enters through the extratubular fluid inlet and exits through the extratubular fluid outlet. The top cover on the column top portion of the condenser 125 has an intratubular fluid inlet connected with the piping 123 and the rear cover at the bottom of the condenser 125 has an intratubular fluid outlet connected to the piping 129. In the condenser 125, the heat exchanger tubes 173 are connected between the upper tubesheet 174 and the lower tubesheet 175 so that no substantial protrusions of heat exchanger tubes 173 occur on the surface, with which the distillate comes into contact, of at least the upper tubesheet 174 out of the upper tubesheet 174 and the lower tubesheet 175, as shown in FIG. 6 or FIG. 7.

The above water separator 127 is made of SUS 304 and, within the same, a diaphragm (baffle plate) 131 is provided. Two sections, namely section (A) 133 and section (B) 134, are thus formed by the baffle plate 131. Among them, the section (A) 133, in which the distillate condensed and liquefied in the condenser 125 is stored, is connected, from the bottom thereof, to a byproduct water treatment tank 135 via a piping 137. The treatment tank 135 is connected with a piping 139 for discharging waste water. The lower portion of another section (B) 134 of the water separator 127 is connected with the reaction vessel 101 via a piping 141 and this piping 141 is provided with a control valve (not shown) and joins (is connected with) a piping 145 connected with a dehydrating solvent storage tank 143 for storing a dehydrating solvent to be caused to azeotropy with byproduct water formed in the reaction vessel 101. Before the joining point (on the water separator 127 side), the piping 141 has a circulating pump 142 disposed in the course thereof and, behind the joining point (on the reaction vessel 101 side), a flowmeter 144 is disposed in the course of the piping 141. Furthermore, the above flowmeter 144 is electrically connected with a flow rate measuring system (not shown) for integrating the flow rate measured and calculating the solvent recycling rate.

In the above water separator 127, the feeding pipe 129 has an opening in the liquid phase section in the section (A) and, at the same time, has an opening in the gaseous phase section, which opening comprises a plurality of holes 162 made on the side face of the feeding pipe 129 in the direction opposite to the baffle plate 131. In FIG. 4, the arrows shown within the water separator 127 indicate the directions of flow of the distillate from the opening(s), and a portion including the plurality of holes 162 of the feeding pipe 129 is shown under magnification. The lower portion of the water separator 127 has a diameter smaller than that of the upper portion. Furthermore, a level gauge (A) 136 is provided as a detecting device of an interface between the dehydrating solvent and byproduct water, and a level gauge (B) 138 as a detecting device of a gas/liquid interface between the gaseous phase and the liquid phase (dehydrating solvent). An antigelling agent is caused to act on inside of the level gauge (A) 136 and of the level gauge (B) 138.

In the above water separator, a condenser 128 is attached to the gaseous phase. The dehydrating solvent and volatile (meth) acrylic acid and the like in the gaseous phase in the water separator are sufficiently cooled in the condenser 128, so that they will not be discharged from the system. The condenser 128 is also provided with an opening (so-called vent) and this prevents the pressure of inside of the reaction system from excessively increasing upon heating of the reaction vessel and the meters from being damaged.

In the above embodiment, the reaction vessel 101 is provided with a raw material storage tank 103 for storing a raw material alcohol, a raw material storage tank 105 for storing (meth) acrylic acid and a catalyst storage tank 107 for storing an acid catalyst, each made of a stainless steel (e.g. SUS 304), and a neutralizing agent storage tank 111 for storing a neutralizing agent (aqueous neutralizing agent solution) for the neutralizing treatment of the acid catalyst after the dehydration reaction, which is made of carbon steel (e.g. high carbon steel), respectively connected to the reaction vessel via pipings 113, 115, 117 and 121. The piping 117 is provided with a pump 167. For more effectively producing the effects of the present invention, a polymerization inhibitor storage tank 109, in which a polymerization inhibitor for inhibiting the polymerizaiton within the reaction system (reaction vessel 101) in the dehydration reaction step, is connected to the reaction vessel by piping 119 via a pump 169.

In the above raw material storage tank 105, (meth) acrylic acid generally contains a trace amount of a polymerization inhibitor, for example 0.1% by weight of methoquinone, as added since (meth) acrylic acid can easily polymerize and, in the case of methacrylic acid, for instance, it polymerizes upon a prolonged period of storage or by heat. Further, in FIG. 4, for constantly maintaining the temperature at 30 to 40° C., the apparatus has a constitution such that a circulating route 151 having a pump 116 and an external jacket 150 (thermal insulating means) is provided so that the raw material (meth) acrylic acid can be circulated therethrough while being constantly maintained at 30 to 40° C. for preventing the same from polymerization.

The above raw material storage tank 105, piping 115, pump 116 and circulation route 151 are preferably lined, on the inside surfaces thereof, with an anticorrosive material such as a synthetic resin so that they can be prevented from corrosion by (meth)acrylic acid, which is corrosive. Similarly, the catalyst storage tank 107, piping 117 and pump 167 are preferably lined with an acid resistance material such as Teflon (trademark), vinyl chloride resin or like synthetic resin so that they can be prevented from corrosion by the acid catalyst. A magnetic pump is preferably used as the pump 167. The polymerization inhibitor storage tank 109 as well as antigelling agent storage tanks 147 and 159 are provided with stirring apparatus (not shown). In cases where a powder-form polymerization inhibitor is dissolved in a solvent, sufficient stirring is preferably carried out for attaining complete dissolution. If a solution in which a polymerization inhibitor or antigelling agent is not completely dissolved is transferred by a pump 160, 169 or 179, the pump may be blocked and stopped. Although such a situation can hardly be occurred if the dissolution is sufficient, it is preferred that the pumps 160, 169 and 179 be ones such that even when a somewhat slurry-like liquid is transferred therethrough they can continue to transfer the same smoothly. In cases where the polymerization inhibitor or antigelling agent is transferred in a form dissolved in a solvent, a pump sealed with a chemical-resistant material such as Teflon or Viton (each being a trademark) is preferably used. For obtaining a pump satisfying such conditions, it is best to provide a Mohno pump (manufactured by Heishin Engineering & Equipment Co., Ltd.) with an appropriate seal. The lower portion of the reaction vessel 101 is connected with a piping 153 for recovering the esterification product synthesized by the esterification reaction within the reaction vessel 101.

Figure 5:
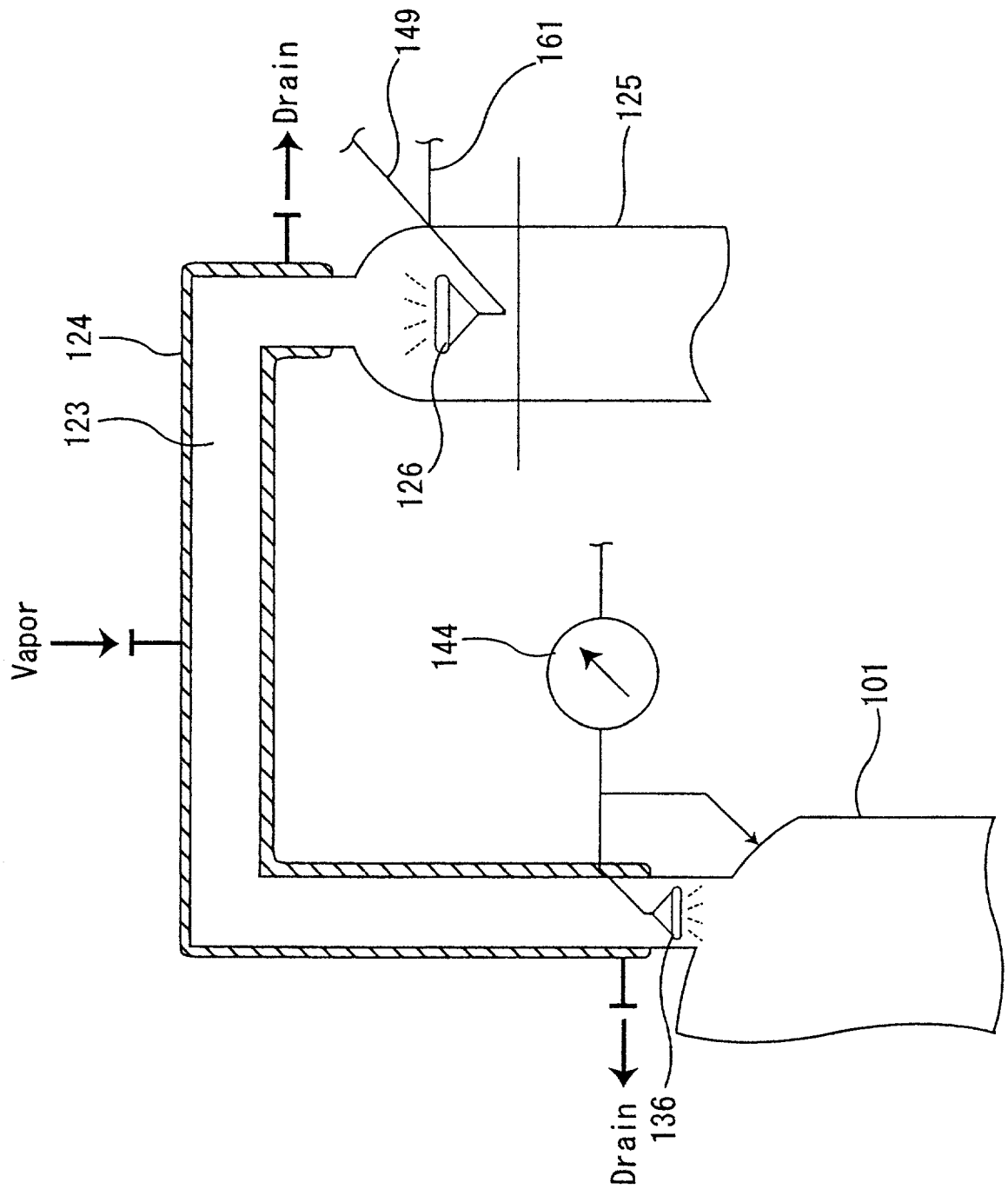
FIG. 5 is a schematic representation of an embodiment each of the spray nozzle to be provided in the vicinity of the part of joining between the reaction vessel and connecting site and the spray nozzle to be provided inside the condenser, which are used in the production method of a dehydration reaction product according to the invention.

In the above embodiment, a spray nozzle 126 is provided in the top portion of the condenser 125 so that the effects of the present invention can be produced effectively. This spray nozzle 126 is connected with the antigelling agent storage tank 147 storing the antigelling agent for preventing the distillate from gelling by means of piping 149 via the pump 179. Similarly, as shown in FIG. 5, a spray nozzle 136 is provided in the vicinity of the connecting site between the reaction vessel 101 and connecting pipe 123 so that spraying can be made from the connecting pipe 123 side toward the reaction vessel 101 side. This spray nozzle 136 is connected with the water separator 127 by means of the piping 141.

The above circulating system is partly utilized also as a circulating system for distilling off the distillate containing the dehydrating solvent from the solution containing the esterification product in the system (the reaction vessel 101) following the dehydration reaction, condensing and liquefying the distillate while inhibiting the formation of a gel-like matter, and removing the distillate containing the dehydrating solvent out of the system. In such circulating system, the water separator 127 is provided with a vacuum pump (ejector) 155 for removing the dehydrating solvent via piping 157 by suction under reduced pressure. Further, in the above embodiment, for producing the effects of the present invention effectively, a spray nozzle 126 newly provided in the column top portion of the condenser 125 is connected by means of a piping 161, with the water-soluble antigelling agent storage tank 159 for storing an aqueous solution of a water-soluble polymerization inhibitor (hereinafter referred to also as "water-soluble antigelling agent" for short) to be utilized in preventing gelation in the aqueous phase in the distillate.

In the above embodiment, a dehydration reaction product is produced in the manner described hereinbelow using the above apparatus constitution.

First, in the dehydration reaction step, the inside of the reaction vessel 101 is charged with the raw material alcohols and (meth) acrylic acid together with the acid catalyst, polymerization inhibitor and dehydration solvent, each in a predetermined amount, from the raw material storage tanks 103 and 105, the catalyst storage tank 107, the polymerization inhibitor storage tank 109 and the dehydration solvent storage tank 143 via the pipings 113, 115, 117 and 119 and the piping 141 connected with the piping 145, respectively, and the esterification reaction is carried out under appropriately selected reaction conditions, inclusive of the reaction temperature, jacket temperature, pressure and so on. The byproduct water formed successively thereby is distilled off, through the connecting pipe 123, as an azeotrope with the dehydrating solvent charged into the reaction vessel 101. For preventing the (meth)acrylic acid from gelling, the capacity A (m$^3$) of the reaction vessel 101 and the total length B (m), on the horizontal basis, of the connecting pipe 123 are selected so that they satisfy the requirement mentioned hereinabove. The gaseous fluid distilled off, namely the solvent-water azeotrope, is passed through and condensed and liquefied in the condenser 125. On that occasion, the gel-like matter formation in the condenser 125 is inhibited since the formation of the distillate liquid retention is suppressed to a sufficient extent on the surface, with which the distillate comes into contact, of at least the upper tubesheet 174 out of the upper tubesheet 174 and the lower tubesheet 175. In the above embodiment, a predetermined amount of the antigelling agent is continuously spayed from the spray nozzle 126 provided in the column top portion of the condenser 125 through the piping 149 from the antigelling agent storage tank 147, to thereby bring the antigelling agent into contact with the distillate occurring as a gaseous fluid and a condensate liquid.

The condensed and liquefied distillate is then collected in the section 133 of the water separator 127 through the piping 129 from the lower portion of the condenser 125 and separated into two phases, namely an aqueous phase and a solvent phase. Among them, the lower layer byproduct water is successively withdrawn from the lower portion of the section 133 through the piping 137 and collected in the byproduct water treatment tank 135. In the treatment tank 135, the water is treated chemically or biologically so as to meet the environmental standard (waste water standard) according to need and then discharged out of this apparatus system through the piping 139. On the other hand, the solvent phase containing the antigelling agent sprayed from the nozzle 126 overflows the diaphragm 131 and is collected in the neighboring compartment 134 in the water separator 127. The solvent phase is refluxed and returned from the lower portion of the section 134 to the reaction vessel 101 through the piping 141 by means of the pump 142 at a predetermined solvent circulation rate. On that occasion, some of that phase is sprayed through the spray nozzle 136 and serves to prevent gelation from occurring in the vicinity of the connecting site between the reaction vessel and the connecting pipe 123.

Further, in the neutralization step, after completion of the dehydration reaction, the temperature is lowered bypassing a cooling medium through the external jacket 102 of the reaction vessel 101 until the inside temperature (liquid temperature) of the reaction vessel 101 is lowered to not higher than 60° C., for instance, and, thereafter, while maintaining the temperature to not higher than the predetermined level by appropriate adjusting, an alkali aqueous solution (neutralizing agent) fed from the neutralizing agent storage tank 111 through the piping 121 as diluted to a predetermined concentration with a large amount of water is added to the reaction vessel 101 to thereby neutralize the acid catalyst and some of (meth)acrylic acid.

After completion of the above neutralization step, the step of distilling off the solvent is carried out by raising the temperature to a predetermined level under ordinary pressure by passing a heating medium (steam under pressure) through the external jacket 102 of the reaction vessel 101, whereby the dehydrating solvent, the water added on the occasion of partial neutralization and the unreacted low-boiling-point raw materials such as (meth) acrylic acid, each occurring in the reaction vessel 101, are distilled off through the connecting pipe 123. In this case, too, while otherwise a gel-like matter may possibly be formed from the unreacted low-boiling-point raw materials such as (meth)acrylic acid, the gel-like matter formation can be satisfactorily inhibited owing to the fact that the capacity A (m$^3$) of the reaction vessel 101 and the total length B (m), on the horizontal base, of the connecting pipe 123 have been selected so as to satisfy the requirement mentioned hereinabove. The solvent-water azeotrope distilled off as a gaseous fluid is passed through the condenser 125 and condensed and liquefied therein. On that occasion, too, the gel-like matter formation in the condenser 125 is inhibited since the formation of the distillate liquid retention is suppressed to a sufficient extent on the surface, with which the distillate comes into contact, of at least the upper tubesheet 174 out of the upper tubesheet 174 and the lower tubesheet 175. As described, the formation of a gel-like matter in the condenser 125 and the like is inhibited.

The distillate condensed and liquefied in the above step of distilling off the solvent is treated in the same manner as the distillate condensed and liquefied in the above-mentioned dehydration reaction step except that the dehydrating solvent distilled off is not refluxed into the reaction vessel 101.

In the above step of distilling off the solvent, a larger amount of water, together with the solvent, enters the condenser 125 as compared with the dehydration reaction step. For preventing the polymerizable compound from forming a gel on the aqueous phase side, a water-soluble antigelling agent is preferably brought into contact with the distillate by continuously dropping, from the spray nozzle 126 provided in the column top portion of the condenser 125, the agent fed from the water-soluble antigelling agent storage tank 159 through the piping 161.

After the above step of distilling off the solvent, water is added for adjustment to the reaction vessel 101 from a water storage tank (not shown) connected to a pipe system (not shown) or from a tap water pipe (not shown) to give an aqueous solution of the desired dehydration reaction product. The aqueous solution of the dehydration reaction product as thus obtained is recovered (for storing) through a piping 153.

EXAMPLES

The following examples illustrate the present invention in further detail. These examples are, however, by no means limitative of the scope of the present invention. Unless otherwise specified, "part(s)" means "part(s) by weight" and "%" means "% by weight".

Example 1

Dehydration Reaction Product Production Example 1

[Esterification]
A cylindrical reaction vessel equipped with a thermometer, a stirrer, two byproduct water separators and two cooling pipes (condensers) was charged with 18,500 parts of methoxypoly(n=25) ethylene glycol, 3,030 parts of methacrylic acid, 240 parts of paratoluenesulfonic acid monohydrate in powder form, 5.5 parts of phenothiazine and 1,090 parts of cyclohexane, and the esterification reaction was carried out at a reaction temperature of 115° C. The reaction vessel had an outside diameter of 30 cm (heated on an oil bath), a height of 50 cm and a capacity (A) of 0.03 m$^3$ and had a structure such that a connecting pipe having an inside diameter of about 2 cm could be connected thereto at a site 10 cm distant from the central axis of the reaction vessel. Each condenser used was a commercially available glass-made Dimroth condenser (condenser pipe length 40 cm; product of Shibata Kagaku Kikai Kogyo). The byproduct water separator and connecting pipe used was a commercially available volumetric water receptacle (capacity 25 ml, equipped with a cock; product of Shibata Kagaku Kikai Kogyo). In this example, the total length (B), on the horizontal basis, of the connecting pipe was 16 cm, the pipe had an ascending gradient of 15° from the reaction vessel side to the condenser side, and the distance from the central axis of the reaction vessel to the central axis of the condenser was 18 cm. Thus, B$^3$/A was 0.137. The relation between B and B$^3$/A in this case is shown in FIG. 3.

The connecting pipe was thermally insulated by covering with aluminum foil. After 60 hours, the esterification conversion was confirmed to have arrived at 99%. To the esterification reaction solution obtained was added, at not higher than 65° C., 1,310 parts of a 4.2% aqueous solution of sodium hydroxide and 3,702 parts of water to thereby neutralize the paratoluenesulfonic acid and some of the methacrylic acid. After neutralization, the temperature was raised to 98° C. and the cyclohexane was distilled off azeotropically with water. After distilling off the cyclohexane, the residue was cooled to give a 80% aqueous solution (M1) of the esterification product. The aqueous solution (M1) obtained was transferred to another container. The condenser and connecting pipe were examined, whereupon no gelation was observed. The aqueous solution (M1) was analyzed by GPC, upon which no peak was found of any high-molecular substance supposed to be a gel precursor.

Comparative Example 1

The same reaction vessel as used in Example 1 was used except that it was equipped with only one byproduct water separator and only one cooling pipe (condenser). In this comparative example, the total length (B), on the horizontal basis, of the connecting pipe was 8 cm. Thus, B$^3$/A was 0.017.

The rate of dehydration in the initial reaction stage was slower as compared with Example 1 and, after 70 hours, the esterification conversion was confirmed to have arrived at 99%. Gel, though in a small amount, was found adhering to the connecting pipe. Upon examination of the aqueous solution (C1) by GPC, peaks ascribable to high-molecular substances presumable to be gel precursors were also found.

Comparative Example 2

The same reaction vessel as used in Example 1 was used except that two byproduct water separators and two cooling pipes (condensers) was fixed at a distance of 70 cm from the central axis of the reaction vessel. In this example, the total length (B), on the horizontal basis, of the connecting pipe was 120 cm. Thus, B$^3$/A was 57.6.

After 70 hours of esterification, the esterification conversion was 97%, and gel was found adhering to the connecting pipe. Upon examination of the aqueous solution (C2) by GPC, peaks ascribable to high-molecular substances presumable to be gel precursors were also found.

Example 2

Dehydration Reaction Product Production Example 2

[Esterification]
A cylindrical reaction vessel equipped with a thermometer, a stirrer, a byproduct water separator and a cylindrical reflux cooling pipe (condenser) and having an external jacket was charged with 36,376 parts of methoxypoly(n=25) ethylene glycol, 10,760 parts of methacrylic acid, 1,470 parts of a 70% aqueous solution paratoluenesulfonic acid hydrate, 11 parts of phenothiazine and 2,344 parts of cyclohexane, and the esterification reaction was carried out at a reaction temperature of 115° C. The reaction vessel had an outside diameter of 3.6 m (including the jacket thickness), a height of 3.8 m and a capacity (A) of 30 m$^3$ and had a structure such that a connecting pipe having an inside diameter of 0.2 m could be connected thereto at a site 1.15 m distant from the central axis of the reaction vessel. The condenser used was a vertical multitubular heat exchanger (fixed tubesheet type) having an outside diameter of 0.9 m and a height of 4 m and containing 624 heat exchanger tubes each having a length of 3.5 m, an outside diameter of 24 mm, and a thickness of 2 mm, the construction of which was such that a solution of an antigelling agent could be sprayed in the column top portion. In this example, the total length (B), on the horizontal basis, of the connecting pipe connecting the reaction vessel to the column top portion of the condenser was 1.55 m, the pipe had an ascending gradient of 57° from the reaction vessel side to the condenser side, and the distance from the central axis of the reaction vessel to the central axis of the condenser was 2.7 m. Thus, B$^3$/A was 0.12. The relation between B and B$^3$/A in this case is shown in FIG. 3.

Separately, a dissolution vessel was charged with 1.1 parts of phenothiazine and 1,087 parts of cyclohexane, and the resulting solution was sprayed from the spray nozzle into the column head space of the condenser using a Mohno pump (manufactured by Heishin Engineering & Equipment Co., Ltd.) during the period from the initiation of refluxing of cyclohexane (inside temperature 107° C.) to the completion of the esterification reaction. The connecting pipe of the reaction vessel was also sprayed with cyclohexane from a spray nozzle to thereby prevent methacrylic acid from polymerizing. After about 20 hours, the esterification conversion was confirmed to have reached 99%. To the esterification reaction solution obtained (50,927 parts) were added, at not higher than 65° C., 6,030 parts of a 4.2% aqueous solution of sodium hydroxide and 5,269 parts of water to thereby neutralize the paratoluenesulfonic acid and some of the methacrylic acid. After neutralization, the temperature was raised to 98° C. and the cyclohexane was distilled off azeotropically with water. During the distilling off of cyclohexane, the antigelling agent solution in the above-mentioned dissolution vessel was sprayed into the column top portion of the condenser. The temperature of the jacket of the connecting pipe was maintained by blowing steam into the jacket from above and discharging the drain and steam from two outlets (on the reaction vessel side and condenser side) in the lower portion thereof. After distilling off the cyclohexane, the residue was cooled to give a 80% aqueous solution (M2) of the esterification product. The aqueous solution (M2) obtained was transferred to another container prepared separately. The above procedure was repeated with 80 batches and, thereafter, the inside of the condenser and of the connecting pipe was examined. No gelation was observed, however. The aqueous solution (M2) was analyzed by GPC, whereupon any peak supposedly due to a high-molecular substance presumable as a gel precursor was not confirmed.

Example 3

A 80% aqueous esterification product solution (M3) was obtained in the same manner as in Example 2 except that no gradient was given to the connecting pipe joining the reaction vessel to the column top portion of the condenser. The aqueous solution (M3) obtained was transferred to another container prepared separately. The above procedure was repeated with 80 batches and, thereafter, the inside of the condenser and of the connecting pipe was examined. Only slight gelation was noticed upon visual observation but the amount thereof was not at such a level that might cause blocking or like problems during the repetitions of 80 batches. The aqueous solution (M3) was analyzed by GPC, whereupon any peak supposedly due to a high-molecular substance presumable as a gel precursor was not confirmed. The relation between B and $B^3/A$ in this case is shown in FIG. 3.

Example 4

A 80% aqueous esterification product solution (M4) was obtained in the same manner as in Example 2 except that the reaction vessel, the condenser and connecting pipe therebetween used were as follows. The reaction vessel had an outside diameter of 1.2 m (including the jacket thickness), a height of 1 m (including the jacket thickness), a capacity (A) of 0.1 $m^3$ and a structure such that a connecting pipe could be connected thereto at a site 0.3 m distant from the central axis of the reaction vessel. The condenser was a vertical multitubular heat exchanger (fixed tubesheet type) having an outside diameter of 0.4 m and a height of 1 m. In this example, the total length (B), on the horizontal basis, of the connecting pipe joining the reaction vessel with the column top portion of the condenser was 1.5 m, the connecting pipe had no gradient between the reaction vessel and condenser, the distance between the central axis of the reaction vessel to the central axis of the condenser was 1.8 m. Thus, $B^3/A$ was 33.8. The relation between B and $B^3/A$ in this case is shown in FIG. 3.

The aqueous solution (M4) obtained was transferred to another container prepared separately. The inside of the condenser and of the connecting pipe was inspected. No gel was found. The aqueous solution (M4) was analyzed by GPC, whereupon any peak supposedly due to a high-molecular substance presumable as a gel precursor was not confirmed.

Example 5

Dehydration Reaction Product Production Example 3

[Amidation]

The same reaction apparatus as used in Example 1 was charged with 6,000 parts of diethylenetriamine and 7,309 parts of adipic acid, and the mixture was stirred and blended in a nitrogen atmosphere. The temperature of the reaction mixture was raised to 150° C. and, while removing the byproduct water resulting from polycondensation, the reaction was carried out for 20 hours to give 11,332 parts of a polycondensate (the byproduct water amounting to 1,977 parts). Then, 17 parts of hydroquinone methyl ether and 701 parts of methacrylic acid were charged, and the amidation reaction was carried out at a reaction temperature of 150° C. After 10 hours of the amidation reaction, 160 parts of byproduct water was removed in the byproduct water separator and 11,890 parts of a polyamide polyamine was obtained. The whole amount of this polyamide polyamine was dissolved in 9,124 parts of water to give 21,014 parts of an aqueous polyamide polyamine solution. A 20,134 parts of this polyamide polyamine solution was charged into an autoclave, the temperature was raised to 5° C., 5,596 parts of ethylene oxide was introduced thereinto over 2 hours, followed by 2 hours of further maturation at 50° C. Thereupon, 25,730 parts of a 66% aqueous amidation product solution (M5) was obtained. The aqueous solution (M5) obtained was transferred to another container. Upon examination of the condenser and connecting pipe, no gel was detected. The aqueous solution (M5) was analyzed by GPC, whereupon any peak supposedly due to a high-molecular substance presumable as a gel precursor was not confirmed.

The reactant compositions and reaction conditions, the esterification conversions, the reaction vessels and connecting pipes used in the production of the esterification product and the situations of gel formation after production as found in Examples 1 to 4 and the Comparative Examples are shown below in Table 1. The reactant composition, the reaction conditions, the reaction vessel and connecting pipe used in the production of the amidation product and the situation of gel formation as found in Example 5 are shown below in Table 2.

TABLE 1

|  | Example | | | | Compar. Ex. | |
| --- | --- | --- | --- | --- | --- | --- |
|  | 1 | 2 | 3 | 4 | 1 | 2 |
| Reactant composition (parts by weight) | | | | | | |
| Methoxypoly(n = 25)ethylene glycol | 18500 | 36376 | 36376 | 36376 | 18500 | 18500 |
| Methacrylic acid | 3030 | 10760 | 10760 | 10760 | 3030 | 3030 |

TABLE 1-continued

|  | Example | | | | Compar. Ex. | |
|---|---|---|---|---|---|---|
|  | 1 | 2 | 3 | 4 | 1 | 2 |
| Paratoluenesulfonic acid | 240 | 1470 | 1470 | 1470 | 240 | 240 |
| Cyclohexane | 1090 | 2344 | 2344 | 2344 | 1090 | 1090 |
| Phenothiazine | 5.5 | 11 | 11 | 11 | 5.5 | 5.5 |
| Reaction condition |  |  |  |  |  |  |
| Reaction temperature (° C.) | 115 | 115 | 115 | 115 | 115 | 115 |
| Reaction time (hrs) | 60 | 20 | 20 | 20 | 70 | 70 |
| Esterification conversion (%) | 99 | 99 | 99 | 99 | 99 | 97 |
| Reaction vessel |  |  |  |  |  |  |
| Capacity A (m$^3$) | 0.03 | 30 | 30 | 0.1 | 0.03 | 0.03 |
| Connecting pipe |  |  |  |  |  |  |
| Length (m) on the horizontal basis | 0.08 | 1.55 | 1.55 | 1.5 | 0.08 | 0.6 |
| Number of pipes | 2 | 1 | 1 | 1 | 1 | 2 |
| Total length B (m) on the horizonal basis | 0.16 | 1.55 | 1.55 | 1.5 | 0.08 | 1.2 |
| Gradient (°) | 15 | 0.57 | 0 | 0 | 15 | 15 |
| Formula (1) |  |  |  |  |  |  |
| B$^3$/A | 0.137 | 0.12 | 0.12 | 33.8 | 0.017 | 57.6 |
| Gel |  |  |  |  |  |  |
| Visual observation | None | None | Found | None | Found | Found |
| GPC | None | None | None | None | Found | Found |

TABLE 2

|  |  | Example 5 |
|---|---|---|
| Reactant composition (parts by weight) | Material to be condensed (amine) | 11332 |
|  | Methacrylic acid | 701 |
|  | Hydroquinone methyl ether | 17 |
| Reaction condition | Reaction temperature (° C.) | 150 |
|  | Reaction time (hrs) | 10 |
| Reaction vessel | Capacity A (m$^3$) | 0.03 |
| Connecting pipe | Length (m) on the horizontal basis | 0.08 |
|  | Number of pipes | 2 |
|  | Total length B (m) on the horizonal basis | 0.16 |
|  | Gradient (°) | 15 |
| Formula (1) | B$^3$/A | 0.137 |
| Gel | Visual observation | None |
|  | GPC | None |

Example 6

Dehydration Reaction Product Production Example 4

[Esterification]

A cylindrical reaction vessel equipped with a thermometer, a stirrer, a byproduct water separator and a vertical multitubular heat exchanger (condenser) and having an external jacket was charged with 36,376 parts of methoxypoly(n=25)ethylene glycol, 10,760 parts of methacrylic acid, 1,470 parts of a 70% aqueous solution of paratoluenesulfonic acid hydrate, 11 parts of phenothiazine and 2,344 parts of cyclohexane, and the esterification reaction was carried out at a reaction temperature of 115° C. The reaction vessel used had a straw bag shape comprising a cylinder having an inside diameter of 3.0 m and a height of 3.8 m, with the upper and lower portions being shaped elliptical (2:1). The capacity of the reaction vessel was about 30 m$^3$. The reaction vessel was equipped with an external jacket capable of being heated with steam or hot water, a stirring apparatus equipped with three retreated blades in each of two stages ((upper stage) blade diameter 1.05 m, blade width 0.12 m, (lower stage) blade diameter 1.65 m, blade width 0.12 m) and baffle rods, a flush valve at the bottom for use in discharging the reaction solution and a manhole and a raw material introducing opening at the upper portion, etc. The material of construction was SUS and the reaction vessel inside and the stirrer was glass-lined. The reaction vessel had a structure such that a connecting pipe having an inside diameter of 0.2 m could be connected thereto at a site 1.15 m distant from the central axis of the reaction vessel. A vertical fixed-tubesheet-type multitubular heat exchanger was constructed and used as the condenser. The condenser had a straw bag shape with a body (shell) inside diameter of 0.85 m, a height of 4.0 m and elliptically curved upper and lower portions (2:1) and included, within the inside, upper and lower tubesheets, 7 baffle plates and 624 heat exchanger tubes (outside diameter 24 mm, inside diameter 20 mm, length 3.5 m), etc. The heat transfer surface area was 161 m$^2$. The material of construction was SUS 304. The welded parts between the upper tubesheet and heat exchanger tubes were all polished so that they were smooth and would not allow liquid retention. The condenser had a structure such that an antigelling agent solution could be sprayed in the column top portion. The length, on the horizontal basis, of the connecting pipe joining the reaction vessel with the column top portion of the condenser was 1.55 m, the connecting pipe had a descending gradient of 0.57° from the reaction vessel side to the condenser side, and the distance between the reaction vessel central axis and the condenser central axis was 2.7 m.

Separately, a dissolution vessel was charged with 1.1 parts of phenothiazine and 1,087 parts of cyclohexane, and the resulting solution was sprayed from the spray nozzle into the column top portion of the condenser using a Mohno pump (manufactured by Heishin Engineering & Equipment Co., Ltd.) during the period from the initiation of refluxing of cyclohexane (inside temperature 107° C.) to the completion of the esterification reaction. The connecting portion of the reaction vessel was also sprayed with cyclohexane from a spray nozzle to thereby prevent methacrylic acid from polymerizing. After about 20 hours, the esterification conversion was confirmed to have reached 99%. To the esterification reaction solution obtained (50,927 parts) were added, at not higher than 65° C. or below, 6,030 parts of a 4.2% aqueous solution of sodium hydroxide and 5,269 parts of water to thereby neutralize the paratoluenesulfonic acid and some of the methacrylic acid. After neutralization, the temperature was raised to 98° C. and the cyclohexane was distilled off azeotropically with water. During the distilling off of cyclohexane, 772 parts of water containing 2 parts of hydroquinone was sprayed into the column top portion of the condenser using a Mohno pump. The temperature of the jacket of the connecting pipe was maintained by blowing steam into the jacket from above and discharging the drain and steam from two outlets (on the reaction vessel side and condenser side) in the lower portion thereof. After distilling off the cyclohexane, the residue was cooled to give an aqueous solution (M6) of the esterification product. The aqueous solution (M6) obtained was transferred to another container prepared separately. The above procedure was repeated with 80 batches and, thereafter, the inside of the condenser and of the connecting pipe was examined. No gelation was observed, however. The aqueous solution (M6) was analyzed by GPC, whereupon any peak supposedly due to a high-molecular substance presumable as a gel precursor was not confirmed.

Comparative Example 3

An aqueous esterification product solution (C3) was obtained in the same manner as in Example 6 except that the welded portions between the upper tubesheet surface and heat exchange tubes were not polished. The aqueous solution (C3) obtained was transferred to another container prepared separately. The above procedure was repeated with 80 batches and then the condenser was examined. The pipe inlet was partly blocked with lumps of a gel.

Example 7

Cement Additive Production Example 1

[Polymerization]

Then, a glass-lined reaction vessel equipped with a thermometer, stirrer, dropping device, nitrogen inlet tube and vertical multitubular heat exchanger (condenser) was charged with 18,122 parts by weight of water, the reaction vessel was purged with nitrogen gas with stirring, and the water was heated to a temperature of 80° C. in a nitrogen atmosphere. Further, while mixing 29,365 weight parts of the aqueous monomer mixture solution (M6) obtained in the above manner and an aqueous solution composed of 223 weight parts of mercaptopropionic acid and 1,323 weight parts of water were added dropwise to the reaction vessel over 4 hours while stirring with a static mixer T8-15-4PT (trademark; product of Noritake) and, simultaneously with the start of this dropping, an aqueous solution of 276 weight parts of ammonium persulfate dissolved in 2,205 weight parts of water as polymerization initiator was added dropwise over 5 hours. After completion of the polymerization initiator dropping, the reaction temperature was further maintained at 80° C. for 1 hour to thereby drive the polymerization reaction to completion. The reaction solution was neutralized to pH 7 by adding 3,660 weight parts of a 49% aqueous solution of sodium hydroxide and 8,608 weight parts of water to give an aqueous polymer solution (P1) with a weight average molecular weight of 20,000 (on the polyethylene glycol equivalent basis determined by gel permeation chromatography (GPC); hereinafter the same shall apply).

The aqueous polymer solution (P1) gave a GPC chart showing no higher molecular weight peaks. A sample of the aqueous polymer solution (P1) was placed in a transparent glass bottle (200 ml) and the appearance thereof was checked by visual observation; no gel was found. No gel accumulation was found in the strainer of the transfer pump.

Example 8

Cement Additive Use Example 1

[Cement Additive]

Mortar test 1

Ordinary portland cement (400 parts; product of Taiheiyo Cement) and 800 parts of standard Toyoura sand were dry-mixed in a Hobart mortar mixer (model N-50; product of Tesco) for 30 seconds, 260 parts of a dilute solution prepared by weighing the specified amount of the cement additive, as indicated in Table 3, and diluting the same with water, and the resulting mixture was kneaded for 3 minutes to give a cement composition (mortar). A hollow cylinder having an inside diameter of 54 mm and a height of 50 mm as placed on a horizontal table was filled to the top with the mortar obtained in the above manner, the cylinder was then gently lifted up vertically, and the major axis and minor axis of the mortar thus allowed to spread on the table were measured. The mean of the axes was reported as the mortar flow value.

Comparative Example 4

Mortar testing was carried out in the same manner as in Example 8 except that no cement additive was used. As shown in Table 3, the mortar flow value was smaller as compared with Example 8 and it was thus established that the flowability was improved by the addition of the cement additive (P1) in Example 8.

TABLE 3

|  | Example 8 | Compar. Ex. 4 |
| --- | --- | --- |
| Cement additive used | Cement additive (P1) | None |
| Level of addition [solid matter] | 0.3 part | — |
| Flow value [mm] | 110 | 70 |

Example 9

Dehydration Reaction Product Production Example 5

[Esterification]

A cylindrical reaction vessel equipped with a thermometer, a stirrer, a byproduct water separator and a vertical multitubular heat exchanger (condenser) and having an external jacket was charged with 18,000 parts of methoxypoly (n=25) ethylene glycol, 3,600 parts of methacrylic acid, 240 parts of paratoluenesulfonic acid monohydrate, 5 parts of phenothiazine and 1,380 parts of cyclohexane, and the esterification reaction was carried out at a reaction temperature of 115° C. The reaction vessel used was the same one as used in Example 6.

Separately, a dissolution vessel was charged with 0.5 part of phenothiazine and 640 parts of cyclohexane, and the resulting solution was sprayed from the spray nozzle into the column top portion of the condenser using a Mohno pump (manufactured by Heishin Engineering & Equipment Co., Ltd.) during the period from the initiation of refluxing of cyclohexane (inside temperature 107° C.) to the completion of the esterification reaction. The connecting pipe of the reaction vessel was also sprayed with cyclohexane from a spray nozzle to thereby prevent methacrylic acid from polymerizing. After about 40 hours, the esterification conversion was confirmed to have reached 99%. To the esterification reaction solution obtained were added, at not higher than 65° C. or below, 2,590 parts of a 4.2% aqueous solution of sodium hydroxide and 2,590 parts of water to thereby neutralize the paratoluenesulfonic acid and some of the methacrylic acid. After neutralization, the temperature was raised to 98° C. and the cyclohexane was distilled off azeotropically with water. During the distilling off of cyclohexane, 350 parts of water containing 1 part of hydroquinone was sprayed into the column head of the condenser using a Mohno pump. The connecting pipe was thermally insulated in the same manner as in Example 6. After distilling off the cyclohexane, the residue was cooled to give an aqueous solution (M7) of the esterification product. The aqueous solution (M7) obtained was transferred to another container prepared separately. The above procedure was repeated with 5 batches and, thereafter, the inside of the condenser and of the connecting pipe was examined. No gelation was observed, however. The aqueous solution (M7) was analyzed by GPC, whereupon any peak supposedly due to a high-molecular substance presumable as a gel precursor was not confirmed.

Comparative Example 5

An aqueous esterification product solution (C4) was obtained in the same manner as in Example 9 except that the welded portions between the upper tubesheet surface and heat exchange tubes were not polished. The aqueous solution (C4) obtained was transferred to another container prepared separately. The above procedure was repeated with 5 batches and then the condenser was examined. Small gel lumps were found adhering to parts of the pipe inlet.

Example 10

Cement Additive Production Example 2

[Polymerization]
Then, a glass-lined reaction vessel equipped with a thermometer, stirrer, dropping device, nitrogen inlet tube and vertical multitubular heat exchanger (condenser) was charged with 8,270 parts by weight of water, the reaction vessel was purged with nitrogen gas with stirring, and the water was heated to a temperature of 80° C. in a nitrogen atmosphere. Further, while mixing 13,430 weight parts of the aqueous monomer mixture solution (M7) obtained in the above manner and an aqueous solution composed of 97 weight parts of mercaptopropionic acid and 600 weight parts of water were added dropwise to the reaction vessel over 4 hours while stirring with a static mixer T8-15-4PT (trademark; product of Noritake) and, simultaneously with the start of this dropping, an aqueous solution of 125 weight parts of ammonium persulfate dissolved in 1,000 weight parts of water as polymerization initiator was added dropwise over 5 hours. After completion of the polymerization initiator dropping, the reaction temperature was further maintained at 80° C. for 1 hour to thereby drive the polymerization reaction to completion. The reaction solution was neutralized to pH 7 by adding 1,060 weight parts of a 49% aqueous solution of sodium hydroxide and 3,700 weight parts of water to give an aqueous polymer solution (P2) with a weight average molecular weight of 20,000.

The aqueous polymer solution (P2) gave a GPC chart showing no higher molecular weight peaks. A sample of the aqueous polymer solution (P2) was placed in a transparent glass bottle (200 ml) and the appearance thereof was checked by visual observation; no gel was found. No gel accumulation was found in the transport pump strainer, either.

Example 11

Cement Additive Use Example 2
[Cement Additive]

Mortar test 2
Ordinary portland cement (800 parts; product of Taiheiyo Cement) and 400 parts of standard Toyoura sand were dry-mixed in a Hobart mortar mixer (model N-50; product of Tesco) for 30 seconds, 200 parts of a dilute solution prepared by weighing the specified amount of the cement additive, as indicated in Table 4, and diluting the same with water, and the resulting mixture was kneaded for 3 minutes to give a cement composition (mortar). A hollow cylinder having an inside diameter of 54 mm and a height of 50 mm as placed on a horizontal table was filled to the top with the mortar obtained in the above manner, the cylinder was then gently lifted up vertically, and the major axis and minor axis of the mortar thus allowed to spread on the table were measured. The mean of the axes was reported as the mortar flow value.

Comparative Example 6

Mortar testing was carried out in the same manner as in Example 11 except that no cement additive was used. As shown in Table 4, the mortar flow value was smaller as compared with Example 11 and it was thus established that the flowability was improved by the addition of the cement additive (P2) in Example 11.

TABLE 4

|  | Example 11 | Compar. Ex. 6 |
| --- | --- | --- |
| Cement additive used | Cement additive (P2) | None |
| Level of addition [solid matter] | 1.6 parts | — |
| Flow value [mm] | 153 | 57 |

Example 12

Dehydration Reaction Product Production Example 6

[Esterification]
A cylindrical reaction vessel equipped with a thermometer, a stirrer, a byproduct water separator and a cylindrical reflux cooling pipe (condenser) and having an external jacket was charged with 12,340 parts of methoxypoly (n=10)

ethylene glycol, 6,000 parts of methacrylic acid, 381 parts of sulfuric acid, 4 parts of phenothiazine and 5,300 parts of cyclohexane, and the esterification reaction was carried out at a reaction temperature of 85° C.

The reaction vessel used had an outside diameter of 3.6 m (including the jacket thickness), a height of 3.8 m and a capacity of 30 m³ and had a structure such that a connecting pipe having an inside diameter of 0.2 m could be connected to a site 1.15 m distant from the central axis of the reaction vessel. The condenser used was a vertical multitubular heat exchanger (fixed tubesheet type) having an outside diameter of 0.9 m and a height of 4 m and containing 624 heat exchanger tubes each having a length of 3.5 m, an outside diameter of 24 mm and a thickness of 2 mm, and having a structure such that an inhibitor solution could be sprayed into the column top portion.

The water separator was a cylindrical vessel and had a structure composed of an upper portion and a lower portion and equipped with a feeding pipe and a baffle plate as well as a level gauge (A) and a level gauge (B), as shown in FIG. 10. The material of construction thereof was SUS 304. The upper portion had a height of 2.6 m and an inside diameter of 2.2 m and the lower portion had a height of 0.36 m and an inside diameter of 0.2 m. The baffle plate was a flat plate and disposed at a position of 0.55 m from the central axis of the cylinder so that it might be positioned 2 m high from the upper portion bottom. Further, the feeding pipe was a round tube having an inside diameter of 25 mm, with a discharge opening into the liquid phase being provided at a site 0.4 m high from the upper portion bottom and a discharge opening into the gaseous phase, which comprises 4 round holes having a diameter of 13 mm (½ inch) and disposed on a vertical line at equal intervals, being provided on the side opposite to the baffle plate at a level 30 to 100 mm higher than the expected interface between the gaseous phase and liquid phase. The level gauges (A) and (B) each had a nozzle so that an antigelling agent could be injected thereinto.

Separately, a dissolution vessel was charged with 0.5 part of phenothiazine and 578 parts of cyclohexane, and the resulting solution was sprayed from the spray nozzle into the column top portion of the condenser using a Mohno pump (manufactured by Heishin Engineering & Equipment Co., Ltd.) during the period from the initiation of refluxing of cyclohexane (inside temperature 82° C.) to the completion of the esterification reaction. The connecting pipe was also sprayed with cyclohexane from a spray nozzle and 1 part of phenothiazine was added to the level gauges (A) and (B) once per 5 batches to thereby prevent methacrylic acid from polymerizing. After about 24 hours, the esterification conversion was confirmed to have reached 99%. The conversion was monitored from time to time by checking the total amount of the byproduct water. During this reaction, the byproduct water was withdrawn through a control valve while adjusting the amount thereof so that the interface between cyclohexane and water might be maintained in the lower portion of the water separator. The cyclohexane was refluxed from the water separator into the reaction vessel.

To the esterification reaction solution obtained were added, at not higher than 50° C., 967 parts of a 49% aqueous solution of sodium hydroxide and 3,800 parts of water to thereby neutralize the sulfuric acid and some of the methacrylic acid. After neutralization, the temperature was raised to 98° C. and the cyclohexane was distilled off azeotropically with water. During the distilling off of cyclohexane, the antigelling agent solution in the above dissolution vessel was sprayed into the column top portion of the condenser. The temperature of the jacket of the connecting pipe was maintained by blowing steam into the jacket from above and discharging the drain and steam from two outlets (on the reaction vessel side and condenser side) in the lower portion thereof. After distilling off the cyclohexane, the residue was cooled to give an aqueous solution (M8) of the esterification product. The aqueous solution (M8) obtained was transferred to another container prepared separately. The above procedure was repeated with 30 batches. During the 30 repetitions of the procedure, the interface within the water separator was maintained at a constant level with good precision and no bumping was noted. No gelation-due troubles occurred in the level gauges.

Comparative Example 7

An aqueous esterification product solution (C5) was obtained in the same manner as in Example 12 except that the feeding pipe of the water separator had no opening on the side face thereof but had only an opening into the liquid phase. The above procedure was repeated with 30 batches. Bumping occurred twice among them and some of the reaction mixture reached the water separator through the condenser. Therefore, on each occasion, the reaction solution and the dehydrating solvent (cyclohexane) in the water separator were discarded, the dehydration reaction step was stopped and the connecting pipe, condenser and water separator were washed.

Comparative Example 8

An aqueous esterification product solution (C6) was obtained in the same manner as in Example 12 except that an error was made in establishing the initial interface level and, as a result, the interface occurred in the upper portion of the water separator. During the dehydration reaction step, the amount of the byproduct water could not be precisely monitored, hence whether the intended conversion had been achieved or not could not be judged.

Comparative Example 9

An aqueous esterification product solution (C7) was obtained in the same manner as in Example 12 except that phenothiazine (antigelling agent) was not added to either of the level gauge (A) and level gauge (B) of the water separator. The above procedure was repeated with 30 batches. Once among them, a trouble occurred due to gelation in the level gauges (A) and (B) in the step of distilling off the solvent. The interface or liquid level could not be monitored due to sticking of a gel to the respective level gauges.

Example 13

Dehydration Reaction Product Production Example 7

[Amidation]

A cylindrical reaction vessel equipped with a thermometer, stirrer, water separator and cooling pipe (condenser) was charged with 6,000 parts of diethylenetriamine, 7,309 parts of adipic acid, and the mixture was stirred and blended in a nitrogen atmosphere. The cock portion of the water separator was charged with 2 parts of methoquinone as an antigelling agent. The reaction vessel had an outside diameter of 30 cm (heated on an oil bath), a height of 50 cm and a capacity (A) of 0.03 m³ and had a structure such that a connecting pipe having an inside diameter of about 2 cm could be connected thereto at a site 10 cm distant from the central axis of the reaction vessel. The condenser used was a commercially available glass-made Dimroth condenser (condenser pipe length 40 cm; product of Shibata Kagaku Kikai Kogyo). The byproduct water separator and connecting pipe used was a commercially available volumetric water receptacle (capacity 25 ml, equipped with a cock; product of Shibata Kagaku Kikai Kogyo). With this water separator, when the cock is closed, the amount of the byproduct water can be read from marked lines provided on the side glass face, so that it functions also as a level gauge. Thus, the amount of the byproduct water can be checked by reading the marked line indicating the liquid level and, upon arrival of the level at the maximum value-indicating marked line, the byproduct water can be discharged out of the system by turning on the bottom cock; thereafter, the amount of the byproduct water newly formed can be read. The reaction mixture was heated to 150° C. and the reaction was conducted for 20 hours while removing the byproduct water formed by the polycondensation, to give 11,332 parts of a polycondensate (the byproduct water amounting to 1,977 parts) Then, 17 parts of hydroquinone methyl ether and 701 parts of methacrylic acid were charged into the vessel and the amidation reaction was carried out at a reaction temperature of 150° C. As a result of 10 hours of amidation reaction, 160 parts of byproduct water was separated in the byproduct water separator to give 11,890 parts of an amidation product (M9), namely a polyamide polyamine. During the reaction, methacrylic acid contained in the byproduct water would not gelate but the cock could be turned on from time to time to discharge the water; the amount of the byproduct water thus could be monitored.

Comparative Example 10

An amidation product (C8) was obtained in the same manner as in Example 13 except that methoquinone (antigelling agent) was not added to the water separator capable of simultaneously functioning as a level gauge. Upon arrival of the water level at the maximum marked line, the cock was turned on but the byproduct water could not be discharged out of the system due to gel formation in the cock portion. From that time point, the byproduct water amount could no longer be monitored.

The invention claimed is:

1. A production method of a dehydration reaction product which comprises a dehydration reaction step of subjecting a reaction solution containing a polymerizable compound to the dehydration reaction,
   said dehydration reaction step comprising using a dehydration reaction apparatus,
   said dehydration reaction apparatus comprising a reaction vessel, a condenser and a connecting pipe joining said reaction vessel with said condenser and
   satisfying the requirement:

$0.05<(B^3/A)<2$ and $1<A<100$ where A is a capacity ($m^3$) of said reaction vessel and B is a total length (m) of said connecting pipe on the horizontal basis.

2. The production method of a dehydration reaction product according to claim 1,
   wherein said pipe has a positive gradient (θ).

3. The production method of a dehydration reaction product according to claim 1,
   wherein said gradient (θ) is 0.3 to 70°.

4. A production method of a dehydration reaction product to be applied to a production of a polymer for cement additives
   which comprises a dehydration reaction step of using a vertical multitubular heat exchanger in producing the dehydration reaction product from a reaction solution,
   said vertical multitubular heat exchanger exchanging heat between an extratubular fluid and a distillate from said reaction solution and
   having a structure comprising a body having an extratubular fluid inlet and an extratubular fluid outlet, covers provided at both upper and lower ends of said body, tubesheets provided in the vicinity of the both upper and lower ends of inside of said body and a plurality of heat exchanger tubes connected between said tubesheets, and
   no substantial retention areas for said distillate occurring on a connecting site between said tubesheet and said heat exchanger tube, and
   wherein an antigelling agent is caused to act on said distillate when carrying out the dehydration reaction step by exchanging heat between the distillate and the extratubular fluid using said vertical multitubular heat exchanger and said reaction solution contains (meth) acrylic acid and/or a dehydration reaction product derived therefrom.

5. A production method of a dehydration reaction product to be applied to a production of a polymer for cement additives
   which comprises a dehydration reaction step of using a vertical multitubular heat exchanger in producing the dehydration reaction product from a reaction solution,
   said vertical multitubular heat exchanger exchanging heat between an extratubular fluid and a distillate from said reaction solution and
   having a structure comprising a body having an extratubular fluid inlet and an extratubular fluid outlet, covers provided at both upper and lower ends of said body, tubesheets provided in the vicinity of the both upper and lower ends of inside of said body and a plurality of heat exchanger tubes connected between said tubesheets, and
   no substantial protrusions of said heat exchanger tubes occurring on the surface, with which said distillate comes into contact, of at least a tubesheet provided in the vicinity of the upper end out of said tubesheets, and
   wherein an antigelling agent is caused to act on said distillate when carrying out the dehydration reaction step by exchanging heat between the distillate and the extratubular fluid using said vertical multitubular heat exchanger and said reaction solution contains (meth) acrylic acid and/or a dehydration reaction product derived therefrom.

6. The production method of a dehydration reaction product according to claim 1, 4 or 5,
   wherein said dehydration reaction step comprises a step of subjecting a reaction solution containing an alcohol and (meth)acrylic acid to esterification reaction to form an ester and/or a step of subjecting a reaction solution containing an amine and (meth)acrylic acid to amidation reaction to form an amide.

7. A production method of a dehydration reaction product which comprises a dehydration reaction step of subjecting an alcohol and/or an amine with (meth)acrylic acid to esterification and/or amidation in the presence of a dehydrating solvent, said dehydration reaction step comprising using a reaction vessel, condenser and a water separator, said water separator being provided with a feeding pipe connected thereinto from said reaction vessel via said condenser, the water separator having a gaseous phase section and a liquid phase section there within, and said feeding pipe having openings in the gaseous phase section and in the liquid phase section of the water separator, and wherein the opening of said feeding pipe in the gaseous phase section comprises one or a plurality of holes made on the side face of said feeding pipe, said alcohol is represented by the following general formula (1):

$$R^1O(R^2O)_nH \qquad (1)$$

in the formula, $R^1$ represents a hydrocarbon group containing 1 to 30 carbon atoms, $R^2O$ are the same or different and each represents an oxyalkylene group containing 2 to 18 carbon atoms, and n represents an average number of moles added of the oxyalkylene group represented by $R^2O$ and is a number of 0 to 300.

8. A production method of a dehydration reaction product which comprises a dehydration reaction step of subjecting an alcohol and/or an amine with (meth)acrylic acid to esterification and/or amidation in the presence of a dehydrating solvent, said dehydration reaction step comprising using a reaction vessel and a water separator, and said water separator being provided with a feeding pipe connected with said reaction vessel, having a gaseous phase section and a liquid phase section therewithin, having smaller diameter in a lower portion thereof than a diameter in an upper portion, and being so controlled that an interface between the dehydrating solvent and byproduct water is maintained in a lower portion thereof, and wherein said alcohol is represented by the following general formula (1):

$$R^1O(R^2O)_nH \qquad (1)$$

in the formula, $R^1$ represents a hydrocarbon group containing 1 to 30 carbon atoms, $R^2O$ are the same or different and each represents an oxyalkylene group containing 2 to 18 carbon atoms, and n represents an average number of moles added of the oxyalkylene group represented by $R^2O$ and is a number of 0 to 300.

9. A production method of a dehydration reaction product which comprises a dehydration reaction step of subjecting an alcohol and/or an amine with (meth)acrylic acid to esterification and/or amidation in the presence of a dehydrating solvent, said dehydration reaction step comprising using a reaction vessel and a water separator, said water separator being provided with a feeding pipe connected with said reaction vessel, having a gaseous phase section and a liquid phase section therewithin and being provided with a detection device at an interface between the dehydrating solvent and byproduct water and/or a gas/liquid interface, and an antigelling agent being caused to act on inside of said detection device, and wherein said alcohol is represented by the following general formula (1):

$$R^1O(R^2O)_nH \qquad (1)$$

in the formula, $R^1$ represents a hydrocarbon group containing 1 to 30 carbon atoms, $R^2O$ are the same or different and each represents an oxyalkylene group containing 2 to 18 carbon atoms, and n represents an average number of moles added of the oxyalkylene group represented by $R^2O$ and is a number of 0 to 300.

10. The production method of a dehydration reaction product according to claim 1, 4, 5, 8 or 9 further comprising mixing said dehydration reaction product with the other materials to produce a polymer for cement additives.

11. The production method of a dehydration reaction product according to claim 1, wherein said gradient (θ) is 0.5 to 45°.

12. The production method of a dehydration reaction product according to claim 1, wherein said A satisfies the requirement:

$$1<A<50.$$

13. The production method of a dehydration reaction product according to claim 7, wherein the opening of said feeding pipe has a diameter of 1 to 200 mm.

14. The production method of a dehydration reaction product according to claim 7 or 13, wherein said water separator is provided with a baffle plate and the opening of said feeding pipe in the gaseous phase section is in the direction opposite to said baffle plate.

15. A production method of a dehydration reaction product which comprises a dehydration reaction step of subjecting an alcohol and/or an amine with (meth)acrylic acid to esterification and/or amidation in the presence of a dehydrating solvent, said dehydration reaction step comprising using a reaction vessel, condenser and a water separator, said water separator being provided with a feeding pipe connected thereinto from said reaction vessel via said condenser, the water separator having a gaseous phase section and a liquid phase section there within, and said feeding pipe having openings in the gaseous phase section and in the liquid phase section of the water separator, and wherein the opening of said feeding pipe in the gaseous phase section comprises one or a plurality of holes made on the side face of said feeding pipe, said alcohol is represented by the following general formula (1):

$$R^1O(R^2O)_nH \qquad (1)$$

in the formula, $R^1$ represents a hydrocarbon group containing 1 to 30 carbon atoms, $R^2O$ are the same or different and each represents an oxyalkylene group containing 2 to 18 carbon atoms, and n represents an average number of moles added of the oxyalkylene group represented by $R^2O$ and is a number of 0 to 300, and mixing said dehydration reaction product with the other materials to produce a polymer for cement additives.

* * * * *